(12) United States Patent
Hidaka et al.

(10) Patent No.: US 6,294,045 B1
(45) Date of Patent: Sep. 25, 2001

(54) PLASTER AGENT AND METHOD OF PREPARING SAME

(75) Inventors: Osafumi Hidaka, Akikawa; Michisuke Ohe, Hino; Osam Magoshi, Urawa; Toshiyuki Kato, Tokorozawa; Tomoki Sakai, Akishima, all of (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 08/392,399

(22) Filed: Feb. 22, 1995

Related U.S. Application Data

(60) Continuation of application No. 08/188,769, filed on Jan. 31, 1994, now abandoned, which is a division of application No. 08/007,830, filed on Jan. 22, 1993, now Pat. No. 5,336,210, which is a continuation of application No. 07/601,779, filed on Oct. 26, 1990, now abandoned.

(30) Foreign Application Priority Data

| Feb. 28, 1989 | (JP) | 1-45178 |
| Feb. 28, 1989 | (JP) | 1-166040 |
| Jun. 28, 1989 | (JP) | 1-166041 |
| Jun. 28, 1989 | (JP) | 1-166042 |
| Aug. 22, 1989 | (JP) | 1-214162 |
| Feb. 28, 1990 | (WO) | PCT/JP90/00263 |

(51) Int. Cl.$^7$ ................................. C09J 5/00
(52) U.S. Cl. ................ 156/327; 424/448; 428/253; 604/307
(58) Field of Search ................ 156/327; 424/448; 604/307; 428/253

(56) References Cited

U.S. PATENT DOCUMENTS

| 4,292,299 | 9/1981 | Suzuki et al. |
| 4,715,369 | 12/1987 | Suzuki et al. |
| 4,801,458 | * 1/1989 | Hidaka et al. ............ 424/448 |
| 4,915,950 | * 4/1990 | Miranda et al. .......... 424/448 |

FOREIGN PATENT DOCUMENTS

| 5731611 | 2/1982 | (JP) |
| 61293911 | 12/1986 | (JP) |
| 62281816 | 12/1987 | (JP) |
| WO8700046 | 1/1987 | (WO) |
| WO8907429 | 8/1989 | (WO) |

* cited by examiner

Primary Examiner—John J. Gallagher
(74) Attorney, Agent, or Firm—Sughrue, Mion, Zinn, Macpeak & Seas, PLLC

(57) ABSTRACT

A plaster agent comprising a water impermeable or water semipermeable film (layer a), one tackifier layer (layer b) laminated on one surface of said layer a, and another tackifier layer (layer d) laminated on said layer b through an intermediary knitted fabric having a weight per unit area of 10 to 100 g/m$^2$ (layer c) comprising hollow fibers having pores extending therethrough in the outer peripheral direction and containing substantially no medicine internally thereof, and at least one of said layer b and said layer d containing a vaporizable or non-vaporizable medicine.

8 Claims, 2 Drawing Sheets

PLASTER AGENT AND METHOD OF PREPARING SAME

This is a Continuation of application Ser. No. 08/188,769, filed Jan. 31, 1994 (now abandoned), which is a divisional of prior parent application Ser. No. 08/007,830, filed Jan. 22, 1993 (now U.S. Pat. No. 5,336,210), which in turn is a continuation of prior application Ser. No. 07/601,779, filed Oct. 26, 1990 (now abandoned).

TECHNICAL FIELD

The present invention relates to a sustained released pharmaceutical plaster agent for percutaneous administration, and a method of preparing same. More specifically, the present invention relates to a plaster agent comprising a knitted fabric comprising specific hollow fibers and a tackifier (or adhesive) layer containing a medicine or drug and a film, and having a high safety factor, excellent sustained releasability and easy handleability, and to a process for efficiently preparing the same.

The present invention relates to a plaster agent containing nitric acid esters useful for the prophylaxis and amelioration of circulatory diseases, particularly cardiac diseases such as stenocardia and arrhythmia.

The present invention further relates to an estradiol-containing plaster agent useful for the prophylaxis and amelioration of disorders frequently observed in women after menopause, such as menopausal disorders, oestroporosis, and Arzheimer dementia.

The present invention further relates to a buprenorphin-containing plaster agent useful for the relief of pain after surgery, from various cancers, and from myocardial infarctions, and further, from lumbago, chronic articular rheumatism, trauma, and exodontia, in particular the pain accompanying various cancers, and as an anesthesia aid.

BACKGROUND ART

In the development of pharmaceuticals, simultaneously with the development of novel compounds having excellent pharmacological effects, various investigations have been made into changes of the dosage forms and an optimization of the administration forms, to to further enhance the effects of these novel compounds or compounds already used as pharmaceuticals.

For example, to prolong the persistency time of a pharmaceutical with a short half-life period, which is also a parameter of the effective persistency time of a pharmaceutical in the body, the development of slow release preparations has been made, which will enable the pharmacologically effective ingredient to be absorbed by the human body at the minimum effective level or higher and the maximum safe level or lower, i.e., in the effective level region in the blood, over a long time.

As examples of slow release preparations, there are known preparations for a percutaneous absorption such as ointments, sprays and coatings. These preparations are coated by hand onto the skin, and therefore, the dose is not constant, and further, a problem arises in that the ointment may adhere to and contaminate the clothing of the patient.

As measures for alleviating these drawbacks, there are known tape agents and plaster agents which incorporate a predetermined amount of a medicine and are molded to a predetermined size (e.g., see Japanese Unexamined Patent Publications (Kokai) Nos. 57-116011, 58-134020), and the use of the method using the tape agent and plaster agent can solve many problems due to the use of an ointment or spray coating.

Also, when a medicine is percutaneously administered, it is known that the ratio of the liver metabolism, which is the phenomenon whereby the pharmacological effect disappears upon receiving the metabolism of the drug in the liver, can be markedly alleviated compared with the case when the medicine is orally administered, and therefore, a tape agent and plaster agent (hereinafter referred to as plaster agent) is an excellent medicine administration form when the medicine can be percutaneously absorbed.

Nevertheless, frequent use of such a plaster agent has shown that some problems arise with the plaster agent of the prior art.

Among such problems, the most frequent is a skin rash generated at the site at which the plaster agent is plastered to a patient. Generally speaking, a sustained release preparation is frequently administered to a patient with chronic diseases, and therefore, the plaster agent is frequently used over a long term, and thus a skin rash is often generated. Further, a problem arises in that, once a skin rash is generated, the afflicted site is susceptible to a growth of the rash. According to statistics, the generation of a skin rash by a plaster agent occurs in 20 to 50% of all patients.

Another problem of the plaster agent is a change of the medicine level in the blood. The factors causing a change of this level in the blood are complicated, and include the plaster agent, the skin, and the human metabolism functions, and therefore, it is not easy to hold the medicine level in the blood at a constant value.

Still another problem concerns the handleability. More specifically, a skin rash could be more or less alleviated by making the support of the plaster agent as thin as possible, enhancing the flexibility, and making the plaster agent smaller to alleviate a skin rash caused by the plaster, but another problem arises in that it is very difficult to plaster the plaster agent correctly at a predetermined position on the patient. For example, recently, plaster agents containing as an effective component nitric acid esters are widely used as therapeutic agents for circulatory diseases such as stenocardia, but the above-mentioned various problems, particularly the skin rash problems, still remain and, therefore, plaster agents capable of stably maintaining the concentration of medicines in the blood and not having the above-mentioned problems are needed in this field.

On the other hand, as the cause of menopausal disorders, oestoroporosis, and Arzheimer dementia, frequently observed in women after menopause, a reduction of estrogen accompanying the menopause is regarded as important, and estradiol, estriol and derivatives thereof have been clinically applied primarily as oral agents and injections.

When estrogen is frequently used, however, side effects such as an increase in an uterus body cancer are observed, and therefore, it is necessary to enhance the biological availability (hereinafter abbreviated as BA) during use, as much as possible, at a minimum necessary dose, while maintaining a stable medicine level in the blood.

Among various estrogens clinically applied, estradiol is one of the natural estrogens which are inherently synthesized and utilized in the living body, has a pharmacologically high activity, and although considered to be the most suitable estrogen for use as a pharmaceutical from the aspect of safety, it has been little used. This is because estradiol, when administered orally, is rapidly metabolized in digestive organs and the liver and the BA is lowered. To maintain the necessary drug level in the blood, a large amount of estradiol must be administered, but this means that an undesirable large amount of harmful metabolites by products will be produced in the blood.

The loss of the BA in estradiol can be markedly ameliorated by a percutaneous administration, and a stable drug level in blood can be still maintained.

Estradiol and derivatives thereof such as esters are known to be percutaneously absorbed, as disclosed in Japanese Patent Publication (Kokoku) No. 46-5427, Japanese Unexamined Patent Publication (Kokai) No. 57-154122, etc. Particularly, the plaster agent disclosed in Japanese Unexamined Patent Publication (Kokai) No. 57-154122 provides an excellent improvement of the BA and stabilization of the drug level in the blood. Nevertheless, although the estradiol-containing plaster agent compensates for a reduction of estrogen accompanying the menopause, the therapeutical period can last for several months to several years, and therefore, a steadfast compliance by the patient is an essential requirement. Particularly, in the presence of a plaster agent, although an uncomfortable feeling during plastering often exists, a generation of a skin rash is a serious problem, an insufficient consideration of this point has been made in the prior art.

In the prior art as described above, in the case of an oral agent, which requires a relatively lower compliance by the patient, the BA is lower and a generation of side effects is a serious problem, but in the case of a percutaneous absorption type plaster agent with a high BA and a stable medicine level in the blood, the problems of discomfort and a generation of skin rash remain.

To alleviate the feeling of discomfort, which is a drawback of the prior art, preferably the flexibility of the plaster agent is enhanced as much as possible and the size thereof made smaller. If the flexibility is made too high, however, the handling of the plaster agent will become very difficult and will reduce the practical applicability thereof. On the other hand, since the size of the plaster agent is proportional to the amount of medicine absorbed, i.e., the medicine level in the blood, if the necessary medicine level in the blood is determined, some means for enhancing the percutaneous absorbability is essential when making the size of the plaster agent smaller. Accordingly, if an absorption promoter is used for enhancing the percutaneous absorbability of the medicine, a problem arises in that a skin rash will occur more frequently. On the other hand, to alleviate the skin rash, the prior art has investigated a suitable selection of the tackifier and a reduction of a residual monomer or residual solvent in the tackifier, but fundamentally it is preferable to enhance the water vaporizability or gas permeability of oxygen and carbon dioxide of the plaster agent. The mere enhancement of the water vaporizability or gas permeability of the oxygen, however, may reduce the sealability of the plaster agent, and thus reduce the percutaneous absorbability of the medicine.

It is considered that 80% of patients at the late stage of cancer suffer unendurable pain, and currently 50 to 80% thereof are receiving therapy for a removal of the pain.

Recently it is considered that late stage cancer patients, substantially without hope from therapy, should pass their remaining time at home with their families, and accordingly, an analgesic which can be easily administered, has a required effect, and causes little side-effects has been developed.

Generally speaking, a therapy of pain is practiced for three ranks of the WHO cancer pain ladder. Namely, when pain is generated, first a non-opium type analgesic is used, and when this is not sufficient, a weak acting opium type narcotic is used, and when even that is not effective, a strong opium type narcotic is used. The unendurable pains experienced by patients at the late stage of cancer are included in the second step and the third step, and as the drug therapeutical method for a therapy thereof, opium type narcotics are employed.

A representative weak opium type narcotic drug is codeine, and a representative strong opium type narcotic drug is morphine. The strength of the action thereof determines whether the drug is a weak opium type or a strong opium type, but various side effects are also taken into consideration. The side effects of opium type narcotics include nausea, vomiting, sleepiness, constipation, and mental disorders, and further, a drug resistance or habit occurs and diminishes the effects thereof during usage. In view of the seriousness of such side effects, even in the analgesic effect of such an opium type narcotic is high, the use thereof must be carefully considered under the present situation.

To solve these problems of opium type narcotics, attempts to alleviate the side effects by enhancing the analgesic effect by a chemical modification of the opium type narcotics have been made for many years.

One of the synthetic analgesics developed from such an investigation is buprenorphin. Buprenorphin is known to have an analgesic effect 25- to 50-fold of that of morphine, and to exhibit little side effects such as mental disorders, etc. Buprenorphin is commercially available as an injection in Japan, and suppositories have been also developed. Further, in other countries, sublingual tablets are commercially available. Investigations into the development thereof as an ointment have been also made.

Nevertheless, in the preparations of the prior art, problems arises in that the number of administrations is very high, and thus a recurrence of the pain begins unless the medicine is administered at a correct time, and further, the administration method if cumbersome. Also, according to the administration method of the prior art, the change in the drug level in the blood is great.

Buprenorphin is a preferable medicine with fewer side effects than morphine, but side actions similar to morphine will be generated by a continuous usage thereof over a long term.

The mechanism of the generation of side effects has not been clarified, but in view of the dose dependency, it is not preferable to enhance the level in the blood more than is necessary. If continuously used for a long term under the state in which the level in blood becomes higher than is necessary, not only is there an increased probability of this leading to serious side effects, but also there is a fear that, even within a short term, a serious side effect such as respiration suppression may be induced.

DISCLOSURE OF INVENTION

Accordingly, an object of the present invention is to obviate the above-mentioned problems of the prior art by providing a plaster agent having a high safety factor, excellent slow releasability and easy handleability, and a process for efficiently preparing same.

A further object of the present invention is to provide a plaster agent containing nitric acid esters having a high BA, a stable medicine level in the blood and having a high level of patient compliance by remarkably lowering the disadvantages, i.e., an uncomfortable feeling and the generation of a skin rash, of the conventional nitric acid ester-containing plaster agents.

A still further object of the present invention is to provide an estradiol-containing plaster agent having a high BA, a stable medicine level in the blood, and having a high level of patient compliance by remarkably lowering the disadvantages, i.e., an uncomfortable feeling and the generation of a skin rash, of the conventional estradiol-containing plaster agents.

A still further object of the present invention is to provide a buprenorphin preparation which can be administered by a simple method and has a stable medicine level in the blood.

Other objects and advantages of the present invention will be apparent from the following descriptions.

In accordance with the present invention, there is provided a plaster agent comprising a water impermeable or water semipermeable film (layer a), one tackifier layer (layer b) laminated on one surface of said film, and another tackifier layer (layer d) laminated on said layer b through an intermediary knitted fabric having a weight per unit area of 10 to 100 $g/m^2$ (layer c) comprising hollow fibers having pores extending therethrough in the outer peripheral direction and containing substantially no medicine internally thereof, and at least one of said layer b and said layer d containing a vaporizable or non-vaporizable medicine.

BRIEF DESCRIPTION OF DRAWINGS

In FIG. 1, a is a film layer, b a tackifier layer, c a hollow fiber knitted fabric layer, d a tackifier layer, and e a releasable sheet.

FIG. 2 comprising 5 and 7 longitudinal and lateral loops, respectively, and the knitted fabric of FIG. 3 comprising 4 and 6 longitudinal and lateral loops, respectively.

BEST MODE OF CARRYING OUT THE INVENTION

Figure 1:
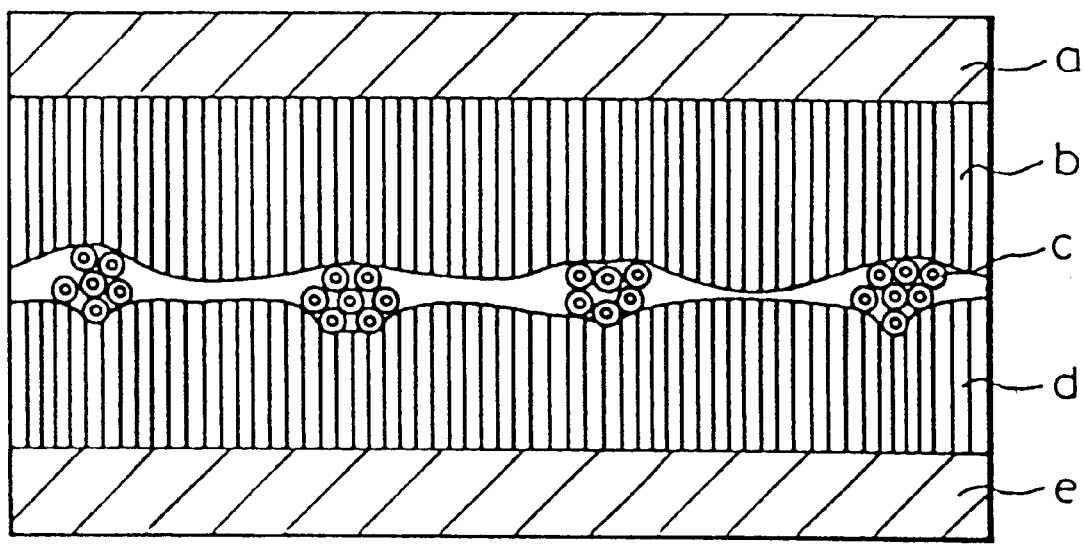
FIG. 1 shows a preferred embodiment of the present invention, and is a sectional view of the sustained release plaster agent obtained in Example 1-1, 2-1, 3-1, 4-1, and 5-1.

As mentioned above, according to the first aspect of the present invention, the object of the present invention can be accomplished by using a knitted fabric comprising hollow fibers having pores extending therethrough in the outer peripheral portion and containing substantially no amount of a medicine, a tackifier layer containing a medicine, and a water impermeable or water semipermeable film, and skillfully utilizing same, to thereby accomplish the present invention.

More specifically, to prevent a skin rash, which is the greatest problem in the use of a plaster agent, and to ensure that no/or substantially no organic solvent used in the preparation steps remains at least in the plaster agent, and that the skin irritation of the tackifier employed is reduced, the plastered site must not be excessively stuffy, and oxygen must be supplied to the plastered site to permit the carbon dioxide and ammonia gas generated by the skin physiology at the plastered site to be permeated.

Particularly, it is important to prevent an excessive stuffiness at the plastered site, which is considered to be related to the difficulty of a permeation of, for example, the oxygen, carbon dioxide, and ammonia.

Nevertheless, from the standpoint of permitting a sufficient amount of a medicine to be absorbed percutaneously, which is the inherent object of a plaster agent, it is essential to allow some stuffiness by sealing the plastered site, and this presents a difficulty in accomplishing the object of the present invention.

The present inventors made an intensive investigation into the stuffy state at which a skin rash occurs, and the stuffy state required for a percutaneous absorption of the medicine, and found that a percutaneous absorption of a medicine will not become rapid even if the stuffiness is increased to the saturated water content of the keratin layer of the skin at the plastered site (at this time superfluous water becomes droplets at the interface between the skin and the plaster agent), and conversely, the skin rash is increased if the water content of the keratin layer exceeds the saturation point. Considering from this that a preferable sealability as the plaster agent maintains the keratin layer of the skin at the plastered site in the vicinity of the saturated water content, the present inventors made an intensive investigation into the dosage form of the plaster agent, and thus accomplished the present invention.

Namely, the present invention provides a plaster agent comprising a water impermeable or water semipermeable film (layer a), one tackifier layer (layer b) laminated on one surface of said film, and another tackifier layer (layer d) laminated on said layer b through an intermediary knitted fabric having a weight per unit area of 10 to 100 $g/m^2$ (layer c) comprising hollow fibers having pores extending therethrough in the outer peripheral direction and containing substantially no medicine internally thereof, and at least one layer of said layer b and said layer d containing a vaporizable or non-vaporizable medicine. Surprisingly, with the plaster agent of the present invention, even if the amount of skin perspiration varies depending on the external environment and the movement of the patient plastered with the plaster agent, the water content in the skin keratin layer at the plastered site can be maintained at substantially the same value.

To prevent a skin rash, preferably the amount of residual solvent in the plaster agent is as small as possible, specifically 100 ppm or less, more preferably 50 ppm or less, of the residual amount of the total solvent used in the preparation of the plaster agent, based on the tackifier weight. In the plaster agent, most of these residual solvents remain when preparing the tackifier layer from a tackifier solution, and as the method of reducing this residual solvent amount, there may be employed the method of heating under a high temperature, the method of vacuum aspiration under heating, the method of washing and extracting the tacky layer with a solvent such as water, methanol, and ethanol; industrially, the method of heating under a high temperature is most frequently employed. Nevertheless, to obtain a tackifier layer with a residual solvent amount of 100 ppm or less, from a tackifier layer (adhesive layer) having a certain thickness and to be used as the tackifier layer of the plaster agent, it is necessary to employ very severe drying conditions.

When a medicine is mixed in the tackifier layer, the employment of such severe conditions may cause a denaturation or decomposition of the medicine, and frequently pose problems, and when a vaporizable medicine is used as the medicine, the medicine is vaporized at a high temperature. Therefore, when such a vaporizable medicine is employed, mild rather than conventional drying conditions must be employed, but it is difficult to thereby obtain a safe plaster agent with little residual solvent therein.

The residual solvent is removed from the tackifier layer at an extremely poor rate if the thickness of the tackifier layer is large, but is relatively easily removed if the thickness of the tackifier layer is small. Accordingly, in the present invention, the tackifier layer containing a medicine comprises two tackifier layers. The following plaster agent of the present invention is described with reference to the processes for the preparation thereof.

The first process for preparing the plaster agent of the present invention comprises:

laminating one tackifier layer (layer b), a knitted fabric having a weight per unit area of 10 to 100 g/m$^2$ (layer c) comprising hollow fibers having pores extending therethrough in the outer peripheral direction and containing substantially no medicine, and another tackifier layer (layer d) on a water impermeable or water semipermeable film, in the order of layers a, b, c, and d, and using a tackifier layer containing a vaporizable or non-vaporizable medicine as at least one of layer b and layer d.

The second preparation process comprises:

(1) impregnating a laminate having a water impermeable or water semipermeable film (layer a), one tackifier layer (layer b) containing substantially no vaporizable medicine or containing a small amount of a vaporizable medicine laminated on a surface of said layer a, and a knitted fabric having a weight per unit area of 10 to 100 g/m$^2$ (layer c) comprising pores extending therethrough in the outer peripheral direction and containing substantially no medicine internally thereof and laminated on said layer b with a medicine solution obtained by dissolving said vaporizable medicine in a volatile solvent on the surface of said layer c, (2) heating said laminate while the surface of said layer c is not in contact with the air, to thereby cause a migration of said vaporizable medicine in said knitted fabric portion to said layer b, (3) laminating the other tackifier layer, (layer d) which may also contain said vaporizable medicine, on said layer c.

The third preparation process comprises:

(1) impregnating a laminate having a water impermeable or water semipermeable film (layer a), one tackifier layer (layer b) containing substantially no vaporizable medicine or containing a small amount of a vaporizable medicine laminated on a surface of said layer a, and a knitted fabric having a weight per unit area of 10 to 100 g/m$^2$ (layer c) comprising pores extending therethrough in the outer peripheral direction and containing substantially no medicine internally thereof and laminated on said layer b with a medicine solution obtained by dissolving said vaporizable medicine in a volatile solvent on the surface of said layer c, (2) laminating the other tackifier layer (layer d), which may also contain said vaporizable medicine, on said layer c to obtain a laminate, (3) heating said laminate to thereby cause a migration of said vaporizable medicine in said knitted fabric portion to said layer b and/or layer d.

The layer d and the layer b may have the same or different thicknesses. Since the thickness of both layers is thinner than that of the total tackifier layer of the final plaster agent, and since severe drying conditions can be applied when no vaporizable medicine is contained, it is easy to bring the residual solvent content to 100 ppm or less, or 50 ppm or less. Further, if necessary, the residual solvent can be reduced by applying heat or a vacuum aspiration, or by extraction and washing. Also, as another residual solvent reducing method, the layers d and b may be prepared by plastering two or more previously prepared thinner tackifier layers.

The first preparation process of the present invention is more specifically described below.

First, the layer b is laminated on one surface of a water impermeable or water semipermeable film. The layer b can be laminated thereon by, for example, coating a tackifier solution on said film, or by pressure adhering said film layer to one surface of the layer b, whereby a laminate comprising the film and the layer b is obtained.

Next, a knitted fabric comprising hollow fibers having pores extending therethrough in the outer peripheral direction and containing substantially no drug is laminated on the layer b.

Thereafter, the layer d is laminated on said knitted fabric (hereinafter called plaster agent raw fabric). The layers d and b may be laminated to the knitted fabric successively as described above, to give a plaster agent with a more stable shape, but the three layers of the layer d, the hollow fiber knitted fabric, and the layer b also may be laminated at the same time.

The layer d and the layer b to be used in the first preparation process of the present invention contain a vaporizable or non-vaporizable medicine in at least one of the layers.

The second and third preparation processes are more specifically described below.

(1) In both of the second and third preparation processes, first a laminate comprising a film, a tackifier layer, hollow fiber knitted fabric impregnated with a medicine solution on the knitted fabric surface is prepared.

First, the layer b containing substantially no medicine or containing a small amount of medicine is laminated on one surface of a water impermeable or water semipermeable film. The lamination method may be carried out by the coating or pressure adhesion of the layer b separately prepared as described above. The amount of medicine in the layer b, in view of the migration of the medicine due to a later heating, can be made substantially zero, or is only a small amount.

Subsequently, on the layer b, a knitted fabric having pores extending therethrough in the outer peripheral direction and containing substantially no medicine is laminated by pressure adhesion to obtain a laminate comprising three layers of a film, the layer b, and a knitted fabric (hereinafter called hollow fiber knitted fabric laminate).

Further, a medicine solution containing a vaporizable medicine of the present invention is dissolved in a volatile solvent such as acetone, methanol, ethanol, and chloroform (hereinafter called medicine solution).

Subsequently, the surface of the knitted fabric of the hollow fiber knitted fabric laminate as described above is impregnated with a predetermined amount of a medicine solution. The volatile solvent may be removed by leaving the laminate to stand under, for example, room temperature conditions, but can be also removed under conditions such as heating or cooling, if necessary.

To obtain a plaster agent uniformly containing a medicine, preferably the knitted fabric is impregnated with a medicine solution, and accordingly, the method of metering and dropwise adding a medicine solution, the method of impregnating a hollow fiber knitted fabric laminate over a predetermined area with a predetermined amount of a medicine solution, the method of metering a medicine solution continuously by a fine cup or pump according to known methods while moving the hollow knitted fabric laminate at a constant speed and permitting a migration thereof when in contact with the knitted fabric, and dropwise adding or spraying same can be employed.

The hollow fiber knitted fabric laminate to be used for impregnation of a medicine solution in the second and third preparation processes of the present invention has a film laminated thereon as described above. Note, even without a lamination of a film, a laminate comprising only the knitted fabric can be impregnated. Nevertheless, when a film is laminated thereon, regardless of the stretchability and the flexibility possessed by said knitted fabric, in this case the film not only imparts a good sealability and a prevention of an escape of the medicine to the plaster agent, but also contributes to the retaining of a constant shape of the knitted fabric, whereby it becomes easier to stably and uniformly impregnate said knitted fabric with a medicine solution, and is suitable for industrial production.

Further, to enhance the uniformity, of the knitted fabrics comprising hollow fibers as described below, a knitted cloth having only a longitudinal knitting and/or reinforced to maintain a constant shape also can be used.

Namely, a hollow fiber knitted fabric laminate impregnated with a medicine solution is obtained.

(2) In the second preparation process of the present invention, the laminate thus obtained is heated while the surface of said knitted fabric is not in contact with the air, to cause a migration of said medicine in said knitted fabric portion into the layer b, and thereafter, the layer d, which may also contain said medicine, is laminated on said knitted fabric.

Here, the state wherein the surface of said knitted fabric is not in contact with the air means specifically that said medicine is under a state in which it cannot escape from the laminate. As such a state, for example, there may be included the rolled state wherein the film is on the outside and the knitted fabric inside, the folded state, or the method of covering or packaging the laminate.

Among them, the method of producing a laminate in a long band with a width of 80 to 1000 mm and rolling the laminate tightly into a roll with the film on the outside is particularly preferable, because the medicine will not be able to easily escape therefrom.

The heating conditions are preferably a temperature of 40 to 80° C. for several hours to several days. Due to this heating, the medicine in said knitted fabric portion is migrated into the layer b, to obtain a layer b containing a vaporizable medicine and a hollow fiber knitted fabric containing substantially no medicine.

Also, due to this heating, the layer b is saturated with the medicine generally within 1 to 2 days, and even if the heating time is prolonged, the medicine amount in the layer b is not increased. Of course, the heating conditions can be controlled depending on the kind of the medicine, for example, by elevating the temperature, whereby the degree of migration into the layer b can be enhanced.

(3) The layer d, which may also contain said varporizable medicine, is laminated on said knitted fabric of the laminate thus obtained by a pressure adhesion, to obtain a plaster agent raw fabric.

Accordingly, the plaster agent raw fabric obtained by the first to third preparation processes of the present invention may be cut, if necessary, and then sealed and packaged to form a plaster agent as the preparation. When it is necessary to accelerate the medicine percutaneous absorption immediately after plastering said plaster agent onto the patient, to thereby expedite the effect by increasing the medicine level in the blood, the sealed and packaged plaster agent is heated at a temperature of 40 to 80° C. for several hours to several days, as required. If the heating conditions are approximately the same as the heating conditions used for the medicine impregnated knitted fabric laminate, the concentrations in the layer d and the layer b will become substantially the same. Further, as the heating conditions are made milder, the initial medicine concentration in the layer d becomes smaller than the medicine concentration in the layer b, whereby the effect on the level in the blood becomes slower, and thus the medicine is released more slowly. Therefore, according to the preparation process of the present invention, it is easier to design a preferable sustained release preparation.

Instead of cutting the plaster agent raw fabric followed by sealing packaging before the heating treatment, it is also possible to directly heat the plaster agent raw fabric to cause a migration of the medicine in the layer b, in an necessary amount, to the tacky layer d.

(2)' Further, according to the third preparation process of the present invention, the layer d, which may also contain said vaporizable medicine, is laminated on the hollow fiber knitted fabric laminate obtained as described above in (1), to obtain a laminate, and (3)' the laminate obtained is then heated to cause a migration of the medicine in said knitted fabric portion into the layer b and/or the layer d, and thus a plaster agent raw fabric is similarly obtained.

Note, the heating conditions in this case are the same as in the second preparation process as described above.

Instead of obtaining the plaster agent raw fabric by migrating, upon heating, a medicine in the knitted fabric portion into the layer b and/or the layer d, after the plaster agent raw fabric is cut and seal-wrapped, the medicine in the knitted fabric portion may be allow to migrate into layer b and/or layer d.

According to the second and third preparation processes, for example, the migration into the layer d is the last step of the preparation steps, whereby a control of the sustained releasability of the vaporizable medicine can be easily attained. Further, when the layer d is laminated after a migration of the medicine in the knitted fabric portion into the layer b, an advantage is gained in that the lamination is carried out because there is no affect by the medicine.

In the present invention, the contents of the medicine contained in the layer b and the layer d may be different, and further, their compositions and additives may be different.

Also, in the present invention, when using the layer d and the layer b with specific thicknesses, and when the knitted fabric of hollow fibers has a specific weight per unit area, a suitable number of voids will occur around the hollow fiber knitted fabric provided at the center of the plaster agent obtained, and through a mutual interaction between the voids and the hollow fibers having pores extending through in the outer peripheral direction, a plaster agent is preferably provided which has no excessive stuffiness at the plastered site and gives a good sealability, whereby a medicine is absorbed as intended by the present invention.

Also, by controlling the loop number of the knitted fabric of hollow fibers, the layer b and the layer d are in good contact with each other whereby, even when a medicine is not contained in the layer d, the medicine is migrated from the layer b to the layer d and there released, to thus obtain a preferable sustained release effect.

The plaster agent raw fabric of the present invention can be any desired size of 3 to 100 $cm^2$, and can be cut to any desired shape such as circular, square, or rectangular, and can be packaged according to a known process, to thereby form a plaster agent for medical use.

The hollow fibers to be used in the present invention must have pores extending therethrough in the outer peripheral direction, and contain substantially no medicine. Here, the hollow fibers having pores extending therethrough in the outer peripheral direction are preferably hollow fibers having fine pores, which are scattered over the whole cross-section of the hollow fiber and arranged in the fiber axis direction, and at least a part of which communicate with the hollow portion.

The external shape and the shape of the hollow portion in the lateral cross-section of the hollow fiber of the present invention may be as desired. For example, the external shape and the hollow portion are approximately circular, either of the external shape and the hollow portion is approximately circular and the other deformed, and the external shape and the hollow portion are both similar or have dissimilar deformed shapes. The size of the external shape is not particularly limited.

The thickness of such a hollow fiber is preferably 0.2 to 20 denier, preferably 1–5 denier or more. When the thickness is 20 denier or more, the skin irritation is very high, but a hollow fiber with a thickness of 0.2 denier or less has a poor handleability.

The hollow ratio of the hollow fiber of the present invention may be as desired, but particularly preferably is 5% or more, and the ratio of the pores extending through in the outer peripheral direction in fiber lateral cross-sectional area excluding the hollow portion is preferably 0.01 to 70%, more preferably 0.01 to 50%, most preferably 1 to 50%.

In the present invention, the hollow fibers must be in the form of a knitted fabric. The knitted fabric may be constituted primarily of the hollow fibers as described above, but fibers other than such hollow fibers also can be partially mixed therein, as long as the effect intended by the present invention is not impaired.

The forms of fabric may be broadly classified into woven fabrics, knitted fabrics, and nonwoven fabrics. Among these fabrics, woven fabrics have been widely used in the art for medical use such as gauze and an adhesive plaster. As indicated above, of the several different forms of fibers generally used in the art, the hollow fibers used in the present invention must be in the form of a knitted fabric. This is primarily because woven fabrics have a good dimensional stability, and are easily handled. Nevertheless, woven fabrics give a greater skin irritation when formed into plaster agents. In contrast, knitted fabrics give little skin irritation, and a thin knitted fabric has even less skin irritation. Particularly, a thin knitted fabric comprising hollow fibers having pores extending therethrough in the outer peripheral direction is extremely flexible and causes substantially no skin irritation. Surprisingly, substantially no flexibility will be lost even when a thin film with little stretchability is laminated on such knitted fabric. This may be because a delicate allowance within the fiber texture absorbs external stress.

The weight per unit area of the knitted fabric of hollow fibers of the present invention is preferably 10 g/m$^2$ to 100 g/m$^2$. If the weight per unit area is too large, the sealability of the plaster agent is worsened, and thus the percutaneous absorbability of the medicine will be poor. On the contrary, if the weight per unit area is too small, various problems will arise, i.e., if the weight per unit area is too small, the knitted fabric is difficult to handle and an excessive sealability sometimes occurs as the weight per unit area becomes smaller.

Further, the knitted fabric of the hollow fibers of the present invention is preferably knitted so as to have loop numbers of 3 to 22/cm in the longitudinal and lateral directions, with the sum thereof being 15 to 37/cm, when a frame with a square opening of 1 cm×1 cm at the center thereof is applied on the knitted fabric and the loops of the knitted fabric are counted.

Figure 2:
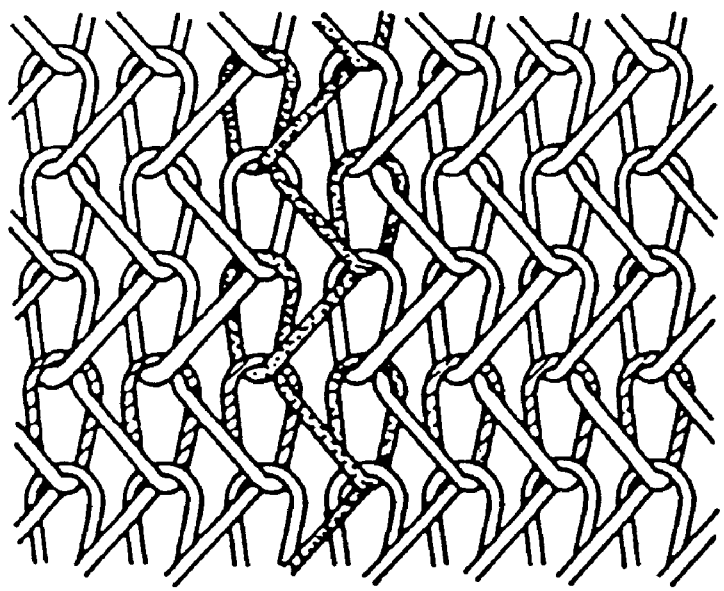
FIG. 2 and FIG. 3 are preferable examples of the texture of the knitted fabric of hollow fibers of the present invention.
Figure 3:
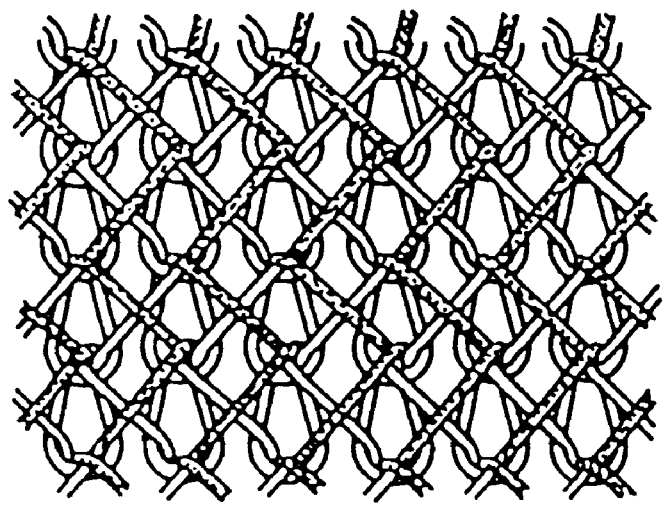

Regarding the texture of the knitted fabric, reference can be made to "Meriyasu Gijutsu Hikkei" (Society of Fiber Machinery of Japan, Aug. 10, 1982). Note, FIG. 6.2 on page 199 and FIG. 4.17 on page 109 of this Journal are shown as FIG. 2 and FIG. 3. In FIG. 2, the numbers of loops in the longitudinal and lateral directions are counted as 7 and 5, respectively, and in FIG. 3, there are 4 loops in the longitudinal direction and 6 in the lateral direction. In the case of FIG. 2 and FIG. 3, the loop number per unit length is not clear, because practical dimensions are not given, but the sums of the loop number at the longitudinal and lateral direction were 24/cm and 20/cm when length of longitudinal and lateral is 0.5 cm×0.5 cm.

In the present invention, if the sum of the loop number of the knitted fabric is 37/cm or more, in addition to the problem of a poor sealability of the plaster agent, the stability of the preparation when the plaster agent is plastered onto the patient will be worsened, whereby an interlayer peeling will occur between the tackifier layer and the fabric.

Particularly preferably, the sum of the loops is 26/cm or less. If the sum of the loops is 15/cm or less, when the weight per unit area of the knitted fabric is relatively smaller, the layer b will extrude through the mesh of the knitted fabric, whereby the tackifier will undesirably stick to machinery and workers handling the hollow fiber knitted fabric laminate. On the other hand, when the weight per unit area of the knitted fabric is relatively larger, the voids around the hollow fiber knitted fabric in the plaster agent become too large, and the sealability becomes poor. Even if the number of loops is the same, by changing the number of hollow fibers used for making one loop, the weight per unit area can be freely changed, but in the present invention, the weight per unit area is preferably 10 to 100 g/m$^2$, and the sum of the loops is preferably 15 to 37/cm, most preferably, theweight per unit area is 20 to 60 g/m$^2$, and the sum of the loops is 15 to 26/cm. Particularly, by using a knitted fabric obtained by stretching a hollow fiber knitted fabric so that the number of loops in the longitudinal direction is 1.5-fold or more that in the lateral direction, instead of the same number of loops in both the longitudinal and lateral directions, the handleability of the hollow fiber knitted fabric is improved to a great extent, and thus a plaster agent having a stable quality and an excellent sustained releasability is obtained.

As the material of the hollow fiber usable in the present invention, any material including, for example, polyesters such as polyethylene terephthalate; polyolefins such as polyethylene, polypropylene; polyamides such as nylon 6, nylon 66; polyurethane, cellulose acetate, polyacrylonitrile, polyvinyl chloride, polyvinyl acetate can be chosen. Among them, polyesters are preferred, and particularly, polyethylene terephthalate is preferred, because of it's high safety to human beings, excellent stability against heat, light and humidity, little mutural interaction wih medicine, difficulty to be modified by a solvent used in the impregnation of a medicine solution to a hollow fiber.

The hollow fiber usable in the present invention can be prepared according to the processes described in, for example, Japanese Unexamined Patent Publication (Kokai) Nos. 56-20612, 56-20613, and 56-43420.

In the present invention, hollow fibers also can be used by combining a plurality of different materials or forms thereof, or using different hollow ratios.

In the present invention, the vaporizable medicine refers to a medicine which is vaporizable when applied to the human body, and therefore, a medicine which is inherently solid and vaporized by sublimation, or which is inherently liquid and is vaporized in that state, may be employed. Examples of such medicines include nitric acid esters such as isosorbide nitrate, nitroglycerine as typical examples, but also there can be exemplified guayazulene, menthol, camphor or salicyclic acid esters such as methyl salicyrate. The amount of the medicine used may be suitably determined depending on the potency of the pharmacological action of the medicine and absorbability by the skin, but is preferably 0.1 to 20% by weight based on the total weight of the tackifier. This medicine may exist in and be mutually mixed with the tackifier layer, or a part thereof may be precipitated as crystals. When the medicine is nitric acid esters, the preferable amount is 8 to 18% by weight and the nitric acid ester-containing plaster agent is preferably prepared by the above-mentioned second or third preparation method, especially the third preparation method.

As the medicine in the present invention, a non-vaporizable medicine may also be employed. The non-vaporizable medicine as mentioned in the present invention refers to a medicine which has little vaporizability when applied to the human body. Among such medicines, percutaneous absorbable medicines are preferred.

As such medicines, there can be included, for example, hormones such as estradiol, progesteron and derivatives thereof; analgesics such as morphine, buprenorphin and derivatives thereof; cardiac agents such as chronidine, nifedipine; etc. These are not limitative, and any non-vaporizable, particularly a non-vaporizable and percutaneous absorbable medicine, may be included. The mount of medicine employed may be suitably determined depending on the potency of the pahrmacological action of the medicine employed, and absorbability by skin, etc., but is preferably 0.1 to 20% by weight based on the total weight of the tackifier. Such a medicine may also be present when mixed with tackifier in the tackifier layer, or a part thereof may be precipitated as crystals.

As the tackifier usable in the present invention, conventional pressure sensitive tackifiers may be employed and can be chosen from among, for example, rubbery viscous compositions composed mainly of, for example, silicone rubber, polyisoprene rubber, styrene-butadiene copolymer rubber, acrylic rubber, natural rubber; vinyl viscous compositions such as polyvinyl alcohol, ethylene-vinyl acetate copolymer; viscous compositions composed mainly of silicone tackifier, polyurethane elastomer, polyester elastomer, polybutadiene elastomer; acrylic resins; and so on. Among them, acrylic resins are preferred, and particularly from the standpoint of less skin irritation, adequate tackiness, adhesiveness, a high degree of internal cohesive force, and an excellent solvent resistance, an acrylic resin comprising a copolymer of (1) at least 80 to 98 mole % of an alkyl (meth)acrylate with an alkyl group having 4 or more carbon atoms and (2) 2 to 20 mole % of acrylic acid and/or methacrylic acid is particularly preferred. Examples of the alkyl (meth)acrylate with an alkyl group having 4 or more carbon atoms include butyl (meth)acrylate, amyl (meth)acrylate, hexyl (meth)acrylate, heptyl (meth)acrylate, octyl (meth)acrylate, nonyl (meth)acrylate, decyl (meth)acrylate, 2-ethylhexyl (meth)acrylate and the like. These tackifiers may be employed either singly or in a combination of two or more kinds thereof.

In the present invention, these tackifiers can be also combined corresponding to the kind of medicine, and by using a combination of a tackifier having a higher compatibility for the layer b, and a tackifier having a less compatibility with the medicine but giving little skin irritation for the layer d, a plaster agent giving little skin irritation and having an excellent slow releasability can be obtained.

The preferable thicknesses of the layer d and the layer b in the present invention are 5 to 100 $\mu$m. If the thickness of the tacky layer is large, the amount of residual solvent is greatly increased, and therefore, most preferably the thickness is 50 $\mu$m or less. On the contrary, if the tacky layer becomes thinner, the adhesion to the human skin and to the knitted fabric and film will be lowered, to lower the stability during usage of the plaster agent, and thus a preferable thickness of the tacky layer is 5 $\mu$m or more, particularly 10 $\mu$m or more. Regarding the layers b and d, the thickness of the layers b and d are preferably 10 to 50 $\mu$m and 10 to 100 $\mu$m, respectively, and preferably the layer b is thinner than the layer d.

As the film to be used in the plaster agent of the present invention, those which satisfy the requirements of obstructing an escape of the medicine, do not lower the adhesion to the skin and do not cause discomfort when adhered to the skin are preferred, and are exemplified by films of polyolefins such as a polyethylene, polypropylene; polyesters such as polyethylene terephthalate; polyamides such as nylon 6, nylon 66; polyvinyl alcohol, vinylidene chloride, polyurethane, and ethylene-vinyl acetate copolymer, and rubber. These films my be used either alone, when combined, or as a laminate.

Among these films, particularly an extremely thin polyethylene terephthalate with a thickness of 4.9 $\mu$m or less is preferable, to ensure a stability against heat and light, a good absorption of the medicine, and absence of a mutual interaction with the medicine. (Hereinbelow, this film is called "packing film" in the present invention.)

In the present invention, a peeling sheet also may be provided on the tackifier layer. The peeling sheet may be a conventional sheet, as exemplified by a paper coated on the surface with a releasable layer.

When estradiol or the derivatives thereof is contained, as a medicine, in the plaster agent of the present invention, the estradiol or the derivatives thereof is preferably contained in the above-mentioned acrylic tackifier layer in an amount of 0.5 to 5% by weight.

Here, estradiol or the derivatives thereof refer to natural estrogen, synthetic estrogen and derivatives thereof, as exemplified by estradiol, estradiol benzoate, estradiol dipropionate, estradiol valerate, and ethynyl estradiol (hereinafter, in the present invention, these estradiols are abbreviated as $E_2$).

The concentration of $E_2$ in the acrylic tackifier layer is an important factor in the percutaneous absorption of the $E_2$ containing plaster agent finally obtained. At a concentration of less than 0.5% by weight, a sufficient percutaneous absorbability can not be obtained, and the percutaneous absorbability becomes substantially proportionally enhanced, as the concentration becomes 0.5% by weight or more, with the increase of the concentration. When the concentration is higher than 10% by weight, however, a further increase in the percutaneous absorbability does not substantially occur, but rather a remarkable crystallization of the $E_2$ in the tackifier layer occurs, and as a result, the percutaneous absorbability is reduced. Thus, at a concentration of higher than 10% by weight, the percutaneous absorbability becomes unpreferably small and the adhesive force of the preparation obtained becomes undesirably poor. The preferable concentration is 1 to 5% by weight.

Moreover, the present inventors frequently found that a plaster agent stored in the form of a known packed plaster agent, in an aluminum bag or the like where the $E_2$ concentration in the tackifier layer is 0.5 to 5% by weight, had a poor percutaneous absorbability, and as a more serious problem, that the percutaneous absorbability was changed to a great extent.

The present inventors made an intensive investigation into the cause of such a change with a lapse of time, by enhancing the percutaneous absorbability of $E_2$, discovered that the crystallization of $E_2$ will markedly change depending on the ambient humidity, and searched for a means to prevent this change. As a result, it was found that (1) the equilibrium water content in the acrylic tackifier, which changes depending on the temperature and humidity, is 0.7 to 1.5% under a room temperature, and that a small amount of water may be sometimes used in a part of the steps for preparing the acrylic tackifier. In that case, the water content in the tackifier layer obtained can exceed 2.0% if the drying conditions when obtaining the tackifier layer by coating and drying the acrylic tackifier are mild. Accordingly, if a tackifier layer with such a water content is used, a crystallization of $E_2$ cannot be prevented even if the plaster agent obtained is double or triple anti-humidity packaged with aluminum packaging, and when the water content is different, the extent and speed of the crystallization will differ in correspondence thereto, whereby a varying of the percutaneous absorbability occurs.

In the present invention, by lowering the water content in the tackifier layer to 0.5% by weight or less, a crystallization of $E_2$ becomes difficult, and further, by lowering the concentration of $E_2$ in the tackifier layer to 5% by weight or less, preferably 3.5% by weight or less, it becomes possible to prevent a change of the absorbability due to a precipitation of the crystals from the plaster agent with a lapse of time.

If the concentration of $E_2$ is 0.5% by weight or less, however, the percutaneous absorbability becomes extremely low, and thus the pharmacological effect is not substantially exhibited.

Therefore, in the present invention, an $E_2$ concentration of 0.5 to 5% by weight and a water content of 0.5% by weight are employed, but preferably, when the $E_2$ concentration (% by weight) is represented by $C_E$ and the water content (% by weight) by $C_W$, a water content represented by the following formula is employed, to thereby provide a very stable plaster agent:

$$C_W \leq 0.6 - 0.1 \times C_E \text{ (with the proviso that}$$

$$C_W \text{ is 0.5 or less)}.$$

As the method of providing the water content of 0.5% by weight or lower in the tackifier layer of the plaster agent of the present invention, there may be employed:

(1) The method in which the water content in said tackifier layer is made 0.5% by weight or less by using a sufficient temperature and time in the drying step when making the estradiol containing acrylic tackifier layer to be used in the present invention, and then, to avoid humidification, quickly forming same into a preparation followed by packaging in an anti-humidity package such as an aluminum bag, under a dehumidified environment;

(2) the method in which the tackifier layer obtained by a conventional method is once placed as such, or after processing, under a humidity reduced environment at a mild heating of 40 to 80° C., or under a reduced pressure, to reduce the water content to 0.5% by weight or less, followed by packaging in an anti-humidity bag such as aluminum bag;

(3) the method in which the plaster agent formed into a preparation is placed under the humidity reduced in environment at a mild heating of 40 to 80° C., or under a reduced pressure, to reduce the water content to 0.5% by weight or less, followed by packaging in an ant-humidity bag such as aluminum bag;

(4) the method in which the plaster agent formed into a preparation is stored together with known drying agents such as silica gel, alumina, and phosphorus compounds, in an anti-humidity bag such as aluminum bag or box. When the above-mentioned methods (1), (2), and (3) are employed, although the water content is made 0.5% by weight or less with much effort, the plaster agent for medical use is placed under various temperatures and humidities, and stresses and a slight water permeation may occur, whereby variances of the quality will occur.

As the anti-humidity packaging material, aluminum foil or a plastic packaging material applied with an aluminum vapor deposit well known in the art may be employed. As the plastic, Teflon, polyvinylidene chloride, polyethylene, high density polyethylene, polyisobutylene, butyl rubber, hydrochloric acid rubber are preferable, but according to the results of an investigation by the present researchers, the thickness of the aluminum foil or the aluminum of aluminum vapor deposition was found to be important. Packaging materials are generally designed from the viewpoint of economy, in addition to a good appearance and handling, and the thickness of the aluminum is frequently 7 $\mu$m or less. For the purpose of the present invention, however the thickness of aluminum is preferably 8 $\mu$ or more, more preferably 9 $\mu$ or more. Another mode of anti-humidity packaging is a packaging canned in tinplate, etc., but this is inconvenient when carried and has a problem of economy, and therefore, is not recommended.

One cause of a skin rash at the site plastered with the plaster agent is the residual solvent remaining in the tackifier layer, and thus, although it is known in the art that various organic solvents used for the preparation of the tackifier layer remain in the obtained tackifier layer, it is important to control the amount of the residual solvent, for a reduction of the generation of a skin rash. According to an investigation made by the present inventors, to significantly reduce the skin rash, the amount of the residual solvent is preferably 100 ppm or less, more preferably 50 ppm or less. The above-mentioned methods (1), (2), (3), (4) can be employed to lower the water content of the present invention, whereby the residual solvent also can be preferably lowered.

In the acrylic tackifier layer containing the $E_2$ of the present invention, it is desirable to use a polyvinyl pyrrolidone. This is because, even though the $E_2$ is contained at about 3% by weight, at which the percutaneous absorbability is optimum, the percutaneous absorbability is still too low, and more important, a precipitation of the $E_2$ as crystals in the tackifier layer occurs with a lapse of time, whereby the percutaneous absorbability is changed. The present inventors made an intensive investigation into a means for enhancing the percutaneous absorbability of the $E_2$, and preventing such a change with a lapse of time, and found that it is effective if a polyvinyl pyrrolidone is contained in an amount of 0.5 to 15% by weight.

The polyvinyl pyrrolidone according to the present invention refers to a polymer a N-vinyl-2-pyrrolidone having a molecular weight of about 100,000 or more (hereinafter abbreviated as PVP in the present invention).

When the polymerization degree of PVP is smaller than this, when PVP is dissolved in the dope (solution of a tackifier dissolved in an organic solvent) when making an acrylic tackifier layer, the dope will be gelled and it will become difficult to prepare a tackifier layer having a uniform thickness. Further, specks of the gelled PVP will exist in a large number in the obtained acrylic tackifier layer, and will have an adverse affect on the effect of promoting a percutaneous absorption of the $E_2$.

A small amount of other monomers or polymers may be copolymerized with the PVP of the present invention, provided that the effect of the present invention still can be obtained.

The PVP is contained in an amount of 0.5 to 15% by weight based on the tackifier in the acrylic tackifier layer. When the amount is more than 15% by weight, the adhesion of the tackifier layer becomes poor, and when less than 0.5% by weight, a required $E_2$ percutaneous absorption promoting effect and crystallization preventive effect cannot be obtained.

The $E_2$ percutaneous absorption promoting effect and the crystallization preventive effect are not limited by the $E_2$ concentration in the tackifier layer, but the effects obtained tend to become greater when the concentration of PVP is higher. With a concentration of 10% by weight or more, the increased effect is lessened, and thus the preferable range is 0.5 to 5% by weight.

In the estradiol-containing plaster agent of the present invention containing PVP in the tackifier layer, by incorporating a specific amount of PVP, a crystallization of $E_2$ is prevented, and thus an excellent percutaneous absorbability is obtained. The present inventors have further found that a plaster agent which is stable for a longer term can be obtained by maintaining the water content in the plaster agent at a certain level or lower.

Therefore, in the plaster agent of the present invention, the water content in the plaster agent is preferably 1% by weight or less, more preferably 0.7% by weight or less. This predetermined amount of water content is incorporated by controlling the drying temperature and time, etc., during the preparation of plaster agent, but for maintaining same over a long term, by further preparing the plaster agent with a water content of 0.2% by weight or less, and sealing same under the dry state within a packaging material having a humidity resistance, the above-mentioned water content of 1% by weight or less can be obtained.

In this case, the presence of a drying agent such as silica gel is also effective.

For such a preparation of the present invention to give a desired percutaneous absorbability, preferably the sealability is maintained such that the water content in the preparation is 0.9% or more, more preferably 1.0% or more, when the preparation is plastered to a patient.

Thus, in the present invention, the $E_2$ and an acrylic tackifier are mixed, preferably with PVP, in the presence of a solvent, and the resultant acrylic tackifier dope is coated by a conventional coating machine and dried, preferably by a specific water content, to remove the solvent, whereby a tackifier layer having a thickness of 5 to 100 $\mu$m and containing the $E_2$ is obtained.

Using the acrylic tackifier layer containing the $E_2$ thus obtained, and estradiol plaster agent raw fabric having a specific thickness and comprising an acrylic tackifier layer having the $E_2$ of the present invention is provided according to the above-mentioned first production process.

This plaster agent raw fabric can be used as $E_2$ containing plaster agent by cutting and appropriate size and shape.

In the plaster agent containing buprenorphin to the present invention, in view of the above-mentioned drawbacks of the prior art, a preparation for administering buprenorphin by a simple administration method, and by a method which provides a stable drug level in the blood and is very safe is provided.

The buprenorphins of the present invention refer to free buprenorphin or pharmaceutically acceptable salts such as buprenorphin hydrochloride and the like. Hereinafter, in the present invention, such buprenorphins are abbreviated as BN.

In the present invention, in such a tackifier, the BN is preferably contained in an amount of 1 to 20% by weight, preferably 5 to 15% by weight, based on the total amount of tackifier.

Generally speaking, as the drug concentration in the pressure sensitive tackifier becomes higher, the releasability of the medicine from the plaster agent is enhanced, but in the case of BN, although the BN releasability is enhanced at a content ratio of 1 to 10% by weight in the tackifier, the BN releasability will be lowered when it exceeds about 10% by weight. Particularly, with a content ratio of less than 1% by weight or more than 20% by weight, the plastering area of the preparation for obtaining the BN level in blood for exhibiting a required pharmacological effect becomes larger in a human being in the former, and in the latter, an increased skin irritation and lower adhesive force due to a crystallization of buprenorphin may occur, whereby the superiority thereof to other administration modes of BN is lost.

On the other hand, the size of the plaster agent for ensuring little skin irritation is about 100 cm$^2$ or less. Also, from the viewpoint of the handleability of the preparation, an extremely small preparation causes problems, and a preferable size of the plaster agent is 3 cm$^2$ or more, preferably 20 to 100 cm$^2$.

In the plaster agent according to the present invention, two tackifier layers, layers d and b, are used as the tackifier layer. Therefore, by incorporating the BN only in the layer d, or by incorporating a higher concentration of the BN in the layer d than in the layer b, the amount of the BN used in the plaster agent can be reduced and, therefore, a BN plaster agent having small side effects, even used for a long time, can be provided.

As a production method of the plaster agent containing BN according to the present invention, the above-mentioned first production method may be mentioned.

Each tackifier layer of the present invention preferably has a thickness of 10 to 100 $\mu$m. When the thickness of the tackifier layer is larger, it becomes difficult to remove the solvent employed in preparation of the tackifier layer, thereby posing a problem of a residual solvent. That is, this residual solvent is a major cause of a skin irritation such as a skin rash. Also when the tackifier layer is too thick, the amount of the tackifier layer exposed on the cut surface of the plaster agent obtained becomes larger, whereby external foreign matter will adhere thereto when plastered for a long time to give a dark contaminated state, which will appear unpleasant to the patients. A preferable thickness is 100 $\mu$m or less. On the contrary, when the tackifier layer is smaller than 15 $\mu$m, the adhesiveness force to the human skin will be greatly lowered, and particularly, if 10 $\mu$m or less it becomes difficult to keep the plaster agent on the human skin stably for a long time. A particularly preferable thickness is 10 to 60 $\mu$m.

As the method of reducing the residual solvent, a stronger drying is carried out during preparation of the tackifier layer, i.e., the drying temperature ×drying time is greater, but in the case of BN it is not preferable to make the drying temperature higher because of the poor thermal stability of BN, and thus to make the residual solvent easily volatilizable, preferably the tackifier layer is as thin as 10 to 60 $\mu$m.

Also, the BN content in the tackifier layer is important. BN content in the present invention refers to that in the whole layer of the plaster agent and to exhibit an analgesic effect by a slow release for a sufficient time, in a human being, the BN content is preferably 0.6 mg or more. On the other hand, 30 mg or more is not preferable from the standpoints of an excessive cost and poor safety. A particularly preferable range is 1 to 15 mg.

The clinical dose of BN is small, and the medicine is percutaneously absorbed with relative ease, in view of the dose. Particularly, a free form without a formation of salt can be easily percutaneously absorbed, and the object can be sufficiently achieved with the plaster agent as described above.

Nevertheless, particularly when the present plaster agent is used for pain removal for patients at the late stage of cancer, since it is used at all times, and for a long term of several years, the plaster agent must be small and yet give a high level dosage in the blood, to obtain a sufficient pain removal.

Accordingly, it is also desirable to use an absorption promoter in the plaster agent of the present invention. Examples of such a promoter include:

(1) surfactants such as nonionic surfactants, amphoteric surfactants, anionic surfactants, cationic surfactants, etc. including polyoxetylene hardened castor oil 10 (hereinafter polyoxyethylene hardened castor oil is abbreviated as HCO), HCO-40, HCO-50, HCO-60, polysolvate 40 (hereinafter polysolvate is abbreviated as Tween$^R$), Tween$^R$-60, Tween$^R$-65, Tween$^R$-80, sorbitane trioleate, sorbitane polyoxyethylene(160) polyoxypropylene(30)-glycol monostearate, sorbitane monopalmitate, sorbitane monolaurate, glycerine monostearate, sodium laurylstearate, lauromacrogall, sorbitane sesquioleate, benzalkonium chloride, benzetonium chloride, (2) amines such as monoethanolamine, diethanolamine, triethanolamine, diisopropanolamine, triisopropanolamine, (3) inorganic alkaline compounds such as sodium hydroxide, potassium hydroxide, calcium hydroxide, sodium hydrogen carbonate, (4) polyvinyl pyrrolidine, propylene glycol, benzyl alcohol, menthol, isosorbide nitrate, dodecylazacycloheptane-2-one, ethanol.

The absorption promoter is preferably used in an amount of 0.1 to 5% by weight based on the tackifier. If less than 0.1% by weight, a sufficient absorption promoting effect cannot be obtained, and if more than 5% by weight, the adhesion of the plaster agent is lowered. Such an absorption promoter may be used alone or as a mixture of one or two or more kinds thereof.

Among such absorption promoters, amines and/or inorganic alkaline compounds are particularly effective when the BN is buprenorphin hydrochloride, and when used in an amount of equivalent mole or less relative to the buprenorphin hydrochloride. Also, when ethanol is used as the absorption promoter, by providing a reservoir of ethanol in the plaster agent and making the dosage form such that ethanol can be released at a substantially constant speed from such a reservoir, the percutaneous absorption amount of BN can be controlled.

The present plaster agent containing BN obtained as mentioned above has an excellent handleability, provides a stable BN level in the blood, and has a high safety factor.

The plaster agent of the present invention also may contain, for example, absorption aids, dissolution aids, diffusion aids, and fillers, if necessary.

As the absorption aid or the diffusion aid usable in the present invention, there can be employed, for example, surfactants such as sodium laurylsulfate, sodium dodecylbenzenesulfonate, sodium alkyldiphenyl ether disulfonate, dioctylsulfosuccinate, polyoxyalkylphenyl ether sulfate ammonium salt; alcohol such as ethanol, glycerine, diethylene glycol, propylene glycol, polyethylene glycol, higher fatty acid alochol; dimethyl sulfoxide and alkylmethyl derivatives; salicylic acid, urea, dimethylacetamide, dimethylformamide, lanolin, allantoin, squalene, carbopol, diisopropyl adipate, lauryl pyrroglutamate, ethyl laurate, methyl nicotinate, sorbitol, pyrrolidone derivatives such as polyvinyl pyrrolidone, dodecyl pyrrolidone, methyl pyrrolidone, olive oil, castor oil, fluid paraffin, petrolatum, gelatin, amino acid, benzyl nicotinate, 1-menthol, camphor, dodecylazacycloheptane-2-one, and the like.

When such a diffusion aid is incorporated together with a vaporizable medicine in a medicine solution, and impregnated to the hollow fiber knitted fabric laminate, even in the case of an insufficient migration to the tacky layer, the migration can be preferably enhanced.

As the filler, there can be included water, titanium oxide, calcium carbonate, gypsum, calcium silicate, aluminum silicate, diatomaceous earth, carbon black, red iron oxide, various dyes and pigments, fluid paraffin, petrolatum, lactose, perfumes, deodorants, powder or molding of synthetic resins such as polyethylene, polypropylene, polyester, and polystyrene.

Industrial Applicability

As explained above, the plaster agent according to the present invention has a structure such that the knitted fabric having a weight per unit area of 10 to 100 g/m$^2$ (layer c) comprising hollow fibers having pores extending therethrough in the outer peripheral direction and containing substantially no medicine internally thereof is placed between tackifier layers (layers b and d), wherein at least one of said layer b and said layer d containing a vaporizable or non-vaporizable medicine. Therefore, the resultant plaster agent can be utilized such that the desired percutaneous absorbability (sustained release) can be provided and that the generation of the skin rash can be remarkably prevented, since the plaster agent gives a very moderate roughness to the portions to which it is applied but an excessive stuffiness is prevented. Furthermore, since the plaster agent according to the present invention uses the specified knitted fabric comprising hollow fibers is used, the plaster agent itself is very flexible, does not substantially irritate the skin, and while maintaining the necessary sealability, has only a small amount of residual solvent, an excellent handleability, and a high safety.

EXAMPLE

The present invention is further described in more detail with reference to Examples. All "parts" in the Examples are parts by weight, and the characteristics shown in Examples were measured according to the following methods.

(i) Water absorption speed test method (according to JIS-L 1018

Fibers were formed into a knitted fabric, which was washed with a 0.3% aqueous solution of an anionic detergent Zab (Kao Sekken) by an electric washing machine for domestic use at 40° C. for 30 minutes, repeatedly for a predetermined number of times, and then dried. The sample obtained was spanned horizontally, and one water drop (0.04 cc) was added from the height of 1 cm, and the time until the water was completely absorbed by the sample, and reflected light could be no longer observed, was measured.

(ii) Water absorption measurement method

The dried sample of knitted fabric was dipped in water for 30 minutes or longer, and then dehydrated by a dehydrating unit of the electric washing machine for domestic use for 5 minutes. The water absorption was determined from the weight of the dried sample and the weight of the sample after dehydration, according to the following formula.

$$\text{Water absorption} = \frac{\text{Sample weight} - \text{Dried sample after dehydration weight}}{\text{Dried sample weight (\%)}}$$

(iii) Method of assaying level of isosorbide nitrate in blood

After a separation of the plasma from 3 ml of sampled blood, it was extracted with 4 ml of N-hexane and concentrated, followed by an addition of ethyl acetate to 100 µl, which was then quantitated by GC-ECD.

(iv) Measurement method of BN level in blood

After a separation of plasma from 1 ml of sample blood, the BN was quantitated by the GC-MS method as described in the Journal of Chromatography, 338 (1985), pp. 89–98.

The hollow fiber and the tackifier solution used in the Examples were prepared according to the following methods.

(1) Hollow fiber sample (1)

An amount of 297 parts of dimethyl terephthalate, 265 parts of ethylene glycol, 53 parts (11.7 mole % based on dimethyl terephthalate) of sodium 3,5-di(carbomethoxy)benzenesulfonate, 0.084 part of manganese acetate tetrahydrate, and 1.22 parts of sodium acetate trihydrate were charged into a glass flask equipped with a rectification tower, subjected to an esterinterchange reaction, and the reaction product after the theoretical amount of methanol was distilled out was charged into a polycondensation flask equipped with a rectification tower. As the stabilizer, 0.090 part of an aqueous 56% normal phosphoric acid was added, 0.135 part of antimony trioxide was added as the polycondensation catalyst, and the reaction was carried out at 275° C. under normal pressure for 20 minutes, under a reduced pressure of 30 mmHg for 15 minutes, under a high vacuum for 100 minutes, and under a final inner pressure of 0.39 mmHg. The copolymerized polymer obtained was found to have an intrinsic viscosity of 0.402 and a softening point of 200° C. After completion of the reaction, the copolymer was formed into chips in a conventional manner.

After 15 parts of the chips of the copolymer and 85 parts of chips of a polyethylene terephthalate having an intrinsic viscocity of 0.640 were mixed in a Nauta mixer (Hosokawa Tekkosho) for 5 minutes, the mixture was dried in a nitrogen gas stream at 110° C. for 2 hours, and further at 150° C. for 7 hours and formed into chips by melting and kneading in a twin screw extruder at 285° C. The chips had an intrinsic viscosity of 0.535 and a softening point of 261° C.

The chips were dried in a conventional manner, and spun by a conventional procedure using a spinning orifice having a circular slit with an arcuate opening 0.05 mm in width and 0.6 mm in diameter, with a two parts being closed, to prepare a hollow fiber with ratio of the outer diameter to the inner diameter thereof of 2:1 (hollow ration 25% ). The original fiber was 300 denier/24 filaments, and the original filament was stretched in a conventional manner at a stretching degree of 4.2-fold to obtain a multi-filament of 71 denier/24 filaments. The multi-filament was formed into a knitted cloth (abbreviated as green cloth), scoured and dried in a conventional manner, followed by treatment with an aqueous 1% caustic soda at boiling point for 2 hours to obtain a cloth thinned 15% of its weight by an alkali treatment of 15%, a water absorption speed of 3 seconds, and a water absorption of 80%. The knitted fabric obtained was stretched 1.5-fold in the longitudinal direction, and heat set at 100° C. for one minute to obtain a knitted fabric with a weight per unit area of 38 g/m². The knitted fabric had loop numbers of 7/cm and 14/cm in the longitudinal and lateral directions respectively.

The fiber obtained was found to be a hollow fiber having fine pores scattered over the whole surface thereof extending toward the axis of the hollow fiber and at least some of which were channeled to the hollow portion of the fiber.

(2) Hollow fiber sample (2)

The knitted cloth obtained in the preparation of the hollow fiber sample (1) which was not subjected to the alkali treatment, and was a knitted fabric with a water absorption speed of 230 seconds and an absorption ratio of 38%. The weight per unit area of the knitted fabric obtained by heat as in the case of the hollow fiber sample (1) is 45 g/cm², and the sum of the loop numbers was the same as for the hollow fiber sample (1).

This hollow fiber had no pores extending therethrough in the outer peripheral direction.

(3) Tackifier solution (1)

An amount of 97.4 parts of 2-ethylhexyl acrylate, 2.5 parts of methacrylic acid, 0.1 parts of a polyethylene glycol (the degree of polymerization 14) dimethacrylate, 1.0 part of benzoyl peroxide, and 100 parts of ethyl acetate were charged into a reactor having a reflux condenser and a stirrer, and polymerization was continued under a nitrogen atmosphere at 60° C. while slowly stirring the mixture for 9 hours. The polymerization conversion was found to be 99.9%.

Then 500 parts of ethyl acetate were added to the polymer solution, to control the solid concentration to about 20%.

Example 1-1

After 13 parts of isosorbide nitrate (ISDN) were added to 500 parts of a tackifier solution (1) with a solid concentration of 20%, the solution was coated on a silicon-coated release paper to a thickness after drying of 20 µm, and dried at 70° C. for 2 minutes, and at 110° C. for 3 minutes. The residual amount of ethyl acetate in the tackifier layer obtained was 49 ppm, and the ISDN content 2.4 g/m². The tacky layer containing the ISDN was divided into three, to obtain 3 tackifier layers with the same composition (called tackifier layer $d_1$, tackifier layer $d_2$, and tackifier layer b).

Next, a film comprising a polyethylene terephthalate and having a thickness of 3.5 µm (see "a" of FIG. 1) was pressure adhered on one surface of the tackifier layer b, and the hollow fiber sample (1) (see "c" of FIG. 1) was pressure adhered on the free surface of said tackifier layer b. The tackifier layer $d_1$ was then pressure adhered on the free surface of the hollow fiber sample (1), and further, the tackifier layer $d_2$ was pressure adhered on the free surface of said tackifier layer $d_1$, to obtain a plaster agent raw fabric containing 8.4 g/m² of ISDN and 45 ppm of a residual solvent.

The thickness of the tackifier layer on the backing side of the present plaster agent was 20 µm (see "b" of FIG. 1) and the thickness of the tackifier layer on the human skin side was 40 µm (see "d" of FIG. 1).

This plaster agent raw fabric was cut to a size of 2 cm×2 cm and plastered on the depilated part of the back of a depilated rat weighing about 180 g, and blood was sampled at predetermined times to measure the ISDN in the plasma. The results are shown in Table 1-1.

Comparative Example 1-1

After 16 parts of ISDN were added to 500 parts of a tackifier solution with a solid concentration of 20%, the solution was coated on a silicon-coated release film to a thickness of the tackifier layer after drying of 60 μ, and dried at 70° C. for 1 minute, and at 90° C. for 3 minutes.

The residual amount of ethyl acetate in the tackifier obtained was 153 ppm, and the content of ISDN was 8.7 g/m². When the drying temperatures were made 90° C. for 1 minute and 130° C. for 3 minutes, to reduce the residual amount of ethyl acetate, the content of ISDN became 8.1 g/m². The residual ethyl acetate at this time was 79 ppm.

After a polyethylene terephthalate film with a thickness of 3.5 μm was pressure adhered on one surface of the tackifier, the composite was cut to a size of 2 cm×2 cm, and the plastering test with a rat was conducted in the same manner as in Example 1-1.

The results are shown in Table 1-1. The present preparation was a flimsy film and was very difficult to handle.

Also, in all cases, erythema was clearly seen on the skin of the rat after the test.

Comparative Example 1-2

A plaster agent was obtained in the same manner as in Example 1-1, except that the hollow fiber sample (2) was used instead of the hollow fiber sample (1), and the plastering test with a rat was conducted. The results are shown in Table 1-1.

The present preparation was stiff when compared with the plaster agent of Example 1-1, and erythema was observed on the skin of the rat after the test.

TABLE 1-1

ISDN level in rat blood (average value of n = 3)

Unit (ng/ml)
Plastering time (hrs)

| Preparation | 0 | 1 | 3 | 8 | 24 |
| --- | --- | --- | --- | --- | --- |
| Example 1-1 | 0 | 165 | 284 | 321 | 169 |
| Comparative Example 1-1 | 0 | 520 | 457 | 272 | 164 |
| Comparative Example 1-2 | 0 | 131 | 227 | 301 | 143 |

Examples 1-2–1-3 and Comparative Examples 1-3–1-5

Using the 71 denier/24 filaments shown in the preparation of the hollow fiber sample ( 1 ), knitted fabrics and woven fabrics with different weights per unit area were prepared, and after scouring and drying according to conventional processes, treated with an aqueous 1% caustic soda solution and at boiling point for 2 hours, to obtain knitted fabrics and woven fabrics thinned 15% of its weight by an alkali treatment. Using these knitted and woven fabrics, the rat plastering tests were conducted in the same manner as in Example 1-1, to obtain the results shown in Table 1-2.

From Table 1-2, it is apparent that the plaster agents of the present invention exhibit an excellent slow release property. In contrast, Comparative Example 1-3 could obtain a desired level in the blood, and in Comparative Examples 1-4 and 1-5, erythema was observed on the skin of the rat.

TABLE 1-2

Estradiol level in rat blood (average value of n = 3)

(Unit: ng/ml)

| | Knitted or woven composition | Weight per unit area of knitted or woven fabric after weight reduction | Number of loops (loops/cm) | | | Plastering time (hrs) | | | | |
| --- | --- | --- | --- | --- | --- | --- | --- | --- | --- | --- |
| | | | Longitudinal | Lateral | Sum | 0 | 1 | 3 | 8 | 24 |
| Example 1-2 | Knitted fabric | 52 | 8 | 16 | 24 | 0 | 120 | 223 | 312 | 125 |
| Example 1-3 | " | 26 | 12 | 14 | 26 | 0 | 208 | 317 | 298 | 151 |
| Comparative Example 1-3 | Knitted fabric | 147 | 20 | 27 | 47 | 0 | 62 | 111 | 73 | 17 |
| Comparative Example 1-4*1 | " | 9 | 18 | 20 | 38 | 0 | 381 | 440 | 213 | 85 |
| Comparative Example 1-5*2 | Woven fabric | 34 | — | — | — | 0 | 201 | 298 | 255 | 164 |

*1Handelability of knitted fabric was poor.
*2Preparation was stiff without stretchability.

Test Example 1-1

A placebo preparation containing no ISDN was prepared under the conditions of Examples 1 -1 to 1-3 and Comparative Examples 1-1 to 1 -5, except that the production scale was reduced to one tenth. Further, a placebo preparation of comparative Example 1-6 was made by using a 6 μ polyethylene terephthalate film instead of a 3.5 μ polyethylene terephthalate film used in Comparative Example 1 - 1 . Each preparation was cut to form a 3 cm ×3 cm sized plaster agent, and plastered in the center of the backs of five healthy human adults 20 to 30 years old and weighing from 56 to 72 kg, each sheet being chosen randomly from 9 sheets in total of the respective plaster agents, and the skin rash state 2 days after plastering was judged.

The judgment was 0 for no reaction, 1 for slight erythema, 2 for clear erythema, and 3 for the generation of papula, etc., and the results judged by the total of the scores for the five members are shown in Table 1-3 .

TABLE 1-3

Human plastering test

| Plastering agent | Skin rash (total score of five members) |
|---|---|
| Placebo of Example 1-1 | 2 |
| Placebo of Example 1-2 | 2 |
| Placebo of Example 1-3 | 4 |
| Placebo of Comparative Example 1-1 | 11 |
| Placebo of Comparative Example 1-2 | 8 |
| Placebo of Comparative Example 1-3 | 2 |
| Placebo of Comparative Example 1-4 | 7 |
| Placebo of Comparative Example 1-5 | 10 |
| Placebo of Comparative Example 1-6 | 13 |

From Table 1-3, it can be clearly seen that the plaster agent of the present invention markedly reduces skin rash.

The sample of Comparative Example 1-3 could not give a desired level in the blood, as shown in Table 1-2.

Example 1-4

An ethyl acetate solution containing the tackifier prepared in the "(3) tackifier solution" as described above was coated on a silicon-coated release film (film substrate was a polyethylene terephthalate with a thickness of 75 μm) to a thickness after drying of 20 μm, and 40 μm, dried at 90° C. for 1 minutes and at 130° C. for 3 minutes, to obtain two kinds of tackifier layers, (1) with a thickness of 20 μm and (2) with a thickness of 40 μm. The residual solvent in the tackifier layers was found to be 20 ppm or less.

On one surface of a film of a polyethylene terephthalate with a thickness of 3.5 μm, a width of 1000 mm, and a length of 100 m was adhered the trackifier layer (1) with a width of 980 mm, residual ethyl acetate of 22 ppm, a thickness of 20 μm, and a length of 100 m, and then on the tackifier layer (1) was pressure adhered the hollow fiber sample (1) with a width of 1000 mm and a length of 100 m. The surface of the hollow fiber sample (1) was placed in continuous contact with an acetone solution containing 30% by weight of ISDN, to uniformly impregnate the acetone solution over substantially the whole surface thereof. By passing the band-shaped laminate impregnated with acetone solution thus obtained through air stream at room temperature for 5 minutes, the acetone solvent was substantially completely removed, to give a laminate containing 9 g/m$^2$ of ISDN. The ISDN-impregnated laminate was wound up tightly into a roll, around a paper tube having an inner diameter of 7.6 cm and a width of 1000 mm.

After the roll-shaped ISDN-impregnated knitted fabric laminate was packaged with an aluminum foil having a thickness of about 100 μm, the package was heated under a constant temperature of 70° C. for 24 hours. Due to this heating operation, almost all of the ISDN in the hollow fiber sample was migrated into the tackifier layer (1), as confirmed by sampling.

On the free surface of the hollow fiber sample (1) of the ISDN-impregnated knitted fabric laminate after heating were pressure adhered a new tackifier layer (2) with a residue of ethyl acetate of 38 ppm, a thickness of 40 μm, a width of 980 mm, and a length of 100 m, to obtain a plaster agent raw fabric. The residual ethyl acetate in the raw fabric was 18 ppm, based on the tackifier.

The plaster agent raw fabric was cut to a size of 2 cm ×2 cm, plastered on the depilated part of the back of a rat weighing about 180 g, and blood was sampled at predetermined times for a measurement of the ISDN in the plasma. The results are shown in Table 1-4.

Example 1-5

The plaster agent raw fabric obtained in Example 1-4 was cut to 2 cm ×2 cm, and heat sealed in an aluminum bag, followed by a heat treatment at 40° C. for 2 days. The plaster agent obtained was plastered on the depilated part of the back of a rat weighing about 180 g, and the blood was sampled at predetermined times for a measurement of the ISDN in the plasma. The results are shown in Table 1-4.

Comparative Example 1-7

A plaster agent was obtained in the same manner as in Example 1-4, except that the hollow fiber sample (2) was used instead of the hollow fiber sample (1), and the plastering test with a rat was conducted. The results are shown in Table 1-4.

When the hollow fiber sample (2) was employed, an attempt was made to obtain a knitted fabric surface impregnated uniformly with acetone solution the free surface of the knitted fabric of the hollow fiber sample (2) by a continuous contact thereof with an acetone solution containing 30% by weight on the surface of the knitted fabric, but the continuous system could not be employed because the hollow fiber sample (2) did not absorb the acetone solution. Accordingly, the acetone solution was uniformly sprayed on the free surface of the hollow fiber sample (2). At this time, the variance of the ISDN amount in the hollow fiber sample (2) was clearly larger by 2- to 3 -fold than when employing the hollow fiber sample (1). Also, it must be carefully handled until about 30–50% or more of the whole amount of the acetone in the hollow fiber sample (2) impregnated with ISDN was evaporated, or the content was varied.

Also, after a complete evaporation of the acetone, crystals of the ISDN were adhered to the hollow fiber sample (2), which became brittle and thick, and therefore, only a very weak tackiness was obtained in the pressure adhesion to the tacky layer (2), and thus it was not suitable for a continuous industrial production.

TABLE 1-4

ISDN level in rat blood (average value of n = 3)

| | Unit (ng/ml) Plastering time | | | | |
|---|---|---|---|---|---|
| Preparation | 0 | 1 | 3 | 8 | 24 |
| Example 1-4 | 0 | 150 | 263 | 305 | 181 |
| Example 1-5 | 0 | 294 | 317 | 313 | 120 |
| Comparative Example 1-7 | 0 | 125 | 236 | 289 | 176 |

Examples 1-6 and 1-7 and Comparative Examples 1-8 -1-10

Using the multi-filament of 71 deniers/ 24 filaments shown in the item of preparation of the hollow fiber sample (1), knitted fabrics and woven fabrics with different weights per unit area were prepared, and after scouring and drying in a conventional manner, treated with an aqueous 1% caustic soda solution and at boiling point for 2 hours, to obtain knitted fabrics and woven fabrics thinned 15% of its weight by an alkali treatment. Using these woven and knitted fabrics, the plastering tests with rats were conducted in the same manner as in Examples 1-4, to obtain the results shown in Table 1-5.

TABLE 1-5

ISDN level in rat blood (average value of n = 3)

(Unit: ng/ml)

| | Woven or knitted composition | Weight per unit area of woven or knitted fabric after reduction | Number of loops of knitted fabric | | | Plastering time (hrs) | | | | | Remarks |
|---|---|---|---|---|---|---|---|---|---|---|---|
| | | | Longi-tudinal | Lateral | Sum | 0 | 1 | 3 | 8 | 24 | |
| Example 1-6 | Knitted fabric | 52 | 8 | 16 | 24 | 0 | 121 | 195 | 272 | 112 | |
| Example 1-7 | " | 26 | 12 | 14 | 26 | 0 | 200 | 307 | 312 | 160 | |
| Comparative Example 1-8 | Knitted fabric | 147 | 20 | 27 | 47 | 0 | 52 | 101 | 67 | 15 | |
| Comparative Example 1-9 | " | 9 | 18 | 20 | 38 | 0 | 362 | 402 | 320 | 101 | Handleability of knitted fabric poor and variance great |
| Comparative Example 1-10 | Woven fabric | 34 | — | — | — | 0 | 193 | 282 | 267 | 198 | Preparation had no stretchability and was stiff |

Example 1-8

A plaster agent raw fabric containing ISDN was obtained in the same manner as in Example 1-4, except that a hollow fiber sample having a hollow ratio of 8%, thinned 22% of its weight by an alkali treatment obtained in the preparation method of the hollow fiber sample (1) was used in place of the hollow fiber sample (1).

Using the plaster agent raw fabric obtained, the ISDN in the plasma was measured in the same manner as in Example 1-4, and as a result, the concentrations in the blood were similarly changed and no skin rash or the like was seen at the applied portion.

Example 2-1

After 2.5 parts of estradiol were added to 500 parts of a tackifier solution with a solid concentration of 20%, the solution was coated on a silicon-coated release paper to a thickness after drying of 20 µm, and dried at 70 °C. for 2 minutes, and at 110 °C. for 3 minutes. The residual amount of ethyl acetate in the tackifier layer obtained was 39 ppm, and the estradiol content was 1.5 g/m$^2$. The tacky layer containing said estradiol was divided into three, to obtain 3 tackifier layers with the same composition (called tackifier layer d$_1$, tackifier layer d$_2$, and tackifier layer b).

Next, a film comprising a polyethylene terephthalate and having a thickness of 3.5 µm (see "a" of FIG. 1) was pressured adhered on one surface of the tackifier layer b, and the hollow fiber sample (1) (see "c" of FIG. 1) was pressure adhered on the free surface of said tackifier layer b. The tackifier layer d$_1$ was then pressure adhered on the free surface of said hollow fiber sample (1), and further, the tackifier layer d$_2$ was pressure adhered on the free surface of said tackifier layer d$_1$, to obtain a plaster agent raw fabric containing 1.6 g/m$^2$ of estradiol and 34 ppm of a residual solvent.

The thickness of the tackifier layer (see "b" of FIG. 1) on the backing side of the present plaster agent was 20 µm, and the thickness of the tackifier layer (see "d" of FIG. 1) on the human skin side was 40 µm.

This plaster agent raw fabric was cut to a size of 2 cm ×2 cm and plastered on the depilated part of the back of a depilated rat weighing about 180 g, and blood was sampled at predetermined times to measure the estradiol in the plasma. The results are shown in Table 2-1.

Comparative Example 2-1

After 2.5 parts of estradiol were added to 500 parts of a tackifier solution was a solid concentration of 20%, the solution was coated on a silicon-coated release film to a thickness of the tackifier layer after drying of 60 µm, and dried at 70 °C. for 1 minute, and at 90 °C. for 3 minutes.

The residual amount of ethyl acetate in the tackifier obtained was 172 ppm, and the content was 1.6 g/m$^2$. When the drying temperatures were made 90 °C. for 1 minute and at 130 °C. for 3 minutes, to reduce the residual amount of ethyl acetate, the content of estradiol became 1.6 g/m$^2$. The residual ethyl acetate at this time was 83 ppm.

After a polyethylene terephthalate film with a thickness of 3.5 µm was pressure adhered on one surface of the tackifier, the composite was cut to a size of 2 cm ×2 cm, and the plastering test with a rat was conducted in the same manner as in Example 2-1.

The results are shown in Table 2-1. The present preparation was a flimsy film and was very difficult to handle.

Also, in all the cases, erythema was clearly seen on the skin of the rat after the test.

Comparative Example 2-2

A plaster agent was obtained in the same manner as in Example 2-1, except that the hollow fiber sample (2) was used instead of the hollow fiber sample (1), and the plastering test with a rat was conducted. The results are shown in Table 2-1.

The present preparation was stiff when compared with the plaster agent of Example 2-1, and erythema was observed on the skin of the rat after the test.

TABLE 2-1

Estradiol level in rat blood (average value of n = 3)

| | Unit (ng/ml) Plastering time (hrs) | | | | |
|---|---|---|---|---|---|
| Preparation | 0 | 1 | 3 | 8 | 24 |
| Example 2-1 | 13 | 411 | 607 | 599 | 183 |
| Comparative Example 2-1 | 22 | 780 | 1003 | 566 | 114 |
| Comparative Example 2-2 | 22 | 344 | 540 | 656 | 128 |

Examples 2-2–2-3 and Comparative Examples 2-3-2-5

Using the 71 denier/24 filaments shown in the preparation of the hollow fiber sample (1), knitted fabrics and woven fabrics with different weights per unit area were prepared, and after scouring and drying according to conventional methods, treated with an aqueous 1% caustic soda solution and at the boiling point for 2 hours to obtain knitted fabrics and woven fabrics thinned about 15% of its weight by an alkali treatment. Using these knitted and woven fabrics, the rat plastering tests were conducted in the same manner as in Example 2-1, to obtain the results shown in Table 2-2.

From Table 2-2, it is apparent that the plaster agents of the present invention exhibit an excellent slow release property. In contrast, Comparative Example 2-3 cannot obtain a desired level in the blood, and in Comparative Examples 2-4 and 2-5, erythema was observed on the skin of the rat.

minutes, to obtain an acrylic tackifier layer containing 2.5% by weight of $E_2$.

The residual solvents in the tackifier layers having a thickness of 20 and 40 $\mu$m were found to be 41 ppm and 123 ppm, respectively, and the water contents thereof were 0.7% by weight.

A polyethylene terephthalate film (see "a" of FIG. 1) with a thickness of 3.5 $\mu$m was pressure adhered onto one surface of the 20 $\mu$m tackifier layer obtained ("b" in FIG. 1), the knitted fabric (see "c" in FIG. 1) of the hollow fiber sample (3) of Reference example pressure was adhered onto the free surface opposite to said tackifier layer, and the tackifier layer (see "d" of FIG. 1) with a thickness of 40 $\mu$m as described above was pressure adhered onto the free surface of the knitted fabric, to give a plaster agent raw fabric. After the plaster agent raw fabric was cut to a size of 5 cm$^2$, it was dehumidified according to the method described below, and packaged. That is, the fabric was heated under a pressure of about 5 mmHg or lower, for 24 hours, in a vacuum dryer. After being taken out from the vacuum dryer, while avoiding water absorption, the fabric was placed in a bag of aluminum laminated with polyethylene and having a thickness of the aluminum foil of 12 mm, and heat sealed.

The $E_2$ content in the plaster agent thus obtained was 2.5% by weight based on the tackifier, the water content was 0.17% by weight based on the tackifier layer, and the residual solvent was 20 ppm. The plaster agent had a water content of 0.17% after an elapse of 3 months under a temperature of 40° C. and a humidity of 75% RH, which are

TABLE 2-2

Estradiol level in rat blood (average value of n = 3)

(Unit: ng/ml)

| | Knitted or woven composition | Weight per unit area of knitted or woven fabric after weight reduction | Number of loops (loops/cm) | | | Plastering time (hrs) | | | | |
|---|---|---|---|---|---|---|---|---|---|---|
| | | | Longi-tudinal | Lateral | Sum | 0 | 1 | 3 | 8 | 24 |
| Example 2-2 | Knitted fabric | 52 | 8 | 16 | 24 | 18 | 301 | 511 | 554 | 147 |
| Example 2-3 | " | 26 | 12 | 14 | 26 | 24 | 500 | 763 | 602 | 133 |
| Comparative Example 2-3 | Knitted fabric | 147 | 20 | 27 | 47 | 25 | 140 | 254 | 261 | 54 |
| Comparative Example 2-4[*1] | " | 9 | 18 | 20 | 38 | 11 | 615 | 912 | 519 | 123 |
| Comparative Example 2-5[*2] | Woven fabric | 34 | — | — | — | 16 | 185 | 411 | 520 | 206 |

[*1] Handelability of knitted fabric was poor.
[*2] Preparation was stiff without stretchability.

Example 3-1

Into 100 parts of the acrylic tackifier solution (1) was added the whole amount of a solution of 0.5 part of estradiol ($E_2$) dissolved in 15 parts of methanol, and further, 25 parts of ethyl acetate were added, followed by stirring, to obtain a uniform dope. The dope was coated on a silicon-coated release paper to a thickness after drying of 20 $\mu$m and 40 $\mu$m, and dried at 90° C. for 1 minute and at 120° C. for 2 the conventional short period stability evaluation conditions of pharmaceuticals.

The plaster agent after an elapse for 3 months under 40° C. and 75% RH was plastered onto the back of a 7 weeks old male hairless rat depilated by an electric hair clipper (n =5), the blood was sampled 2 hours, 4 hours, 8 hours, and 24 hours after the plastering, and a serum was separated for an assay of $E_2$ in the serum by radio-immunoassay.

The results of the levels in the blood are summarized in Table 3-1, in terms of the maximum level in blood Cmax and AUC, which is the area under the curve of the level in the blood vs time.

Examples 3-2 –3 -5, Comparative Examples 3-1 –3 -5

Plaster agents were obtained, in the same manner as in Example 3-1, except for changing the $E_2$ concentration and the water content by changing the amount of estradiol ($E_2$) employed, and changing the dehumidification conditions after cutting the plaster agent raw fabric, and after an elapse of 3 months at 40 ° C. and a humidity of 75% RH, tests were conducted with a hairless rat and the results were as shown in Table 3-1.

TABLE 3-1

Evaluation results of plaster agents
(stored at 40° C. and 75% RH for 3 months)

| | Tackifier layer composition | | Level in blood | |
|---|---|---|---|---|
| | $E_2$ concentration (% by weight) | Water content (% by weight) | AUC (pg.hr/ml) | Cmax (pg.hr/ml) |
| Example 3-1 | 2.5 | 0.17 | 11383 | 1032 |
| Example 3-2 | 0.6 | 0.38 | 7251 | 488 |
| Example 3-3 | 0.6 | 0.29 | 12263 | 1116 |
| Example 3-4 | 0.6 | 0.45 | 6606 | 540 |
| Example 3-5 | 4.5 | 0.09 | 10005 | 782 |
| Comparative Example 3-1 | 0.3 | 0.11 | 3640 | 232 |
| Comparative Example 3-2 | 0.6 | 0.82 | 3565 | 236 |
| Comparative Example 3-3 | 2.5 | 0.69 | 4620 | 276 |
| Comparative Example 3-4 | 4.5 | 0.62 | 4106 | 341 |
| Comparative Example 3-5 | 7.0 | 0.14 | 3106 | 180 |
| Comparative Example 3-6 | 2.5 | 1.90 | 1648 | 79 |

From Table 3-1, it can be clearly seen that the plaster agent of the present invention has an excellent stability with a lapse of time, and exhibits excellent AUC and Cmax effects.

Comparative Example 3-6

The plaster agent with an $E_2$ content of 2.5% by weight and a water content based on the tackifier layer of 0.17% obtained in Example 3-1 was placed, without aluminum bag packaging, under the conditions of 40 ° C. and 75% RH for 2 weeks. The water content was 1.9% and $E_2$ was found to be agglomerated in the tackifier layer, and the plastering tests results with hairless rat were very bad, as shown in Table 3-1.

Example 3-6

The plaster agent with an $E_2$ content of 2.5% by weight and a water content based on the tackifier layer of 0.17% obtained in Example 3-1 was packaged in an aluminum bag. At this time, the thickness of the aluminum foil employed in Example 1 was not 12 mm but 7 mm, and 20 bags each containing one sheet of plaster agent per bag were obtained by heat sealing at a seal width of 6 mm, and the change in average water content with a lapse of time under the conditions of 40 ° C. and 75% RH was examined on an average value of 5 sheets each time.

The water content was 0.23% by weight after one month, 0.31% by weight after two months, 0.38% by weight after three months, and 0.44% by weight after 4 months, with the variance being great.

Example 3-7

The plaster agent with an $E_2$ content of 2.5% by weight and a water content based on the tackifier layer of 0.17% obtained in Example 3-1 was placed in the aluminum bag used in Example 3-6, and 1 g of dry silica gel was sealed together with the plaster agent, followed by heat sealing in the same manner as in Example 3-6, to obtain 20 bags of plaster agents. When the change in the water content in the tackifier layer of the plaster agent was monitored in the same manner as in Example 3-6, the water content was 0.17% or less up to 4 months, with the variance being extremely small.

Example 4-1

To a solution of 0.5 part of estradiol ($E_2$) dissolved in 15 parts of methanol (Solution A), a solution of 0.2 part of a PVP having a molecular weight of 1,200,000 (G.A.F., K- 90 ) dissolved in 30 parts of chloroform, and 100 parts of the acrylic tackifier solution (1 ) were added 55 parts of ethyl acetate, and the mixture was vigorously stirred to form a uniform dope. Then, the dope was coated on a silicon-coated release paper to a thickness after drying of 40 µm, and dried at 90 ° C. for 20 minutes to obtain an acrylic tackifier layer containing $E_2$ (2.5% by weight) and PVP (1% by weight).

The above-obtained two tackifier layers (see "b " and "d " of FIG. 1) having a thickness of 40 µm and containing $E_2$ and PVP were prepared and the hollow fiber sample (3 ) was sandwiched between the two tackifier layers and laminated under pressure. After a polyethylene terephthalate film (see "a " of FIG. 1) with a thickness of 3.5 µm was pressure adhered onto one whole surface of one surface of the free tackifier layer, a plaster agent ($E_2$ (2.5% by weight), PVP (1% by weight)) obtained by cutting it to a size of 5 cm$^2$ was evaluated as mentioned above. The results are also shown in Table 4-1. The preparation according to the present invention sufficiently maintains the flexibility of the plaster, and further, has an excellent handleablility.

TABLE 4-1

Evaluation results of plaster agents

| | Concentration in plaster agent (%) | | Adhesive force | Level in blood (pg/ml) | | | | State of skin after removal of |
|---|---|---|---|---|---|---|---|---|
| Test No. | $E_2$ | PVP | (g/12 cm) | 0 hour after plastering | 2 hours | 8 hours | 24 hours | plaster agent |
| Example 4-1 | 2.5 | 1 | 310 | 22 | 1350 | 1005 | 295 | Good without erythema |

Example 5-1

Into 100 parts by weight of the tackifier solution (1) was added a solution of 1.5 parts of buprenorphin dissolved in a mixture of 15 parts of methanol and 270 parts of ethyl acetate, and further, a solution of 0.2 part of HCO- 60 dissolved in 15 parts of ethyl acetate was added, followed by vigorous mixing and stirring, to obtain a uniform solution (dope).

The dope obtained was coated on a silicon-coated peeling sheet to a thickness of the pressure sensitive tackifier layer containing buprenorphin, after drying, of 30 µm, followed by drying at 50 ° C. for 10 minutes, at 70 ° C. for 2 minutes, and at 50 ° C. for 120 minutes. The residual amount of ethyl acetate in the pressure sensitive tackifier layer was found to be 46 ppm, and the content of the buprenorphin was 2.9 g/m$^2$.

The pressure sensitive tackifier layer containing buprenorphin was divided into two, to obtain two pressure sensitive tackifier layers (called b and d) with the same composition.

Next, on one surface of the pressure sensitive tackifier layer b was pressure adhered a polyethylene terephthalate film with a thickness of 3.5 µm, on the free surface of said pressure sensitive tackifier layer b was pressure adhered the hollow fiber sample (1), and on the free surface of said hollow fiber sample (1) (layer c) was pressure adhered the pressure sensitive tackifier layer d. Further, on the free surface of said tackifier layer d was mounted a silicon-coated film as the peeling sheet, to obtain a plaster agent raw fabric containing 2.9 g/m$^2$ of buprenorphin, as shown in FIG. 1.

After said plaster agent raw fabric was cut to a circular shape with a size of 9 cm$^2$, it was plastered on the depilated part of the back of a hairless rat with a body weight of about 180 g, blood samples were taken at predetermined times, and the buprenorphin levels in the plasma were measured. The content in the present plaster agent was 2.6 g and the content ratio was 7.5% by weight. The results are shown in Table 5-1.

Example 5-2

According to the same procedure as in Example 5-1, except for using 1.6 parts of buprenorphin hydrochloride in place of 1.5 parts of buprenorphin and a mixture of 0.2 parts of HCO- 60 and 0.2 parts of diisopropanolamine in place of 0.2 part of HCO- 60, a plaster agent raw fabric containing 2.8 g/m$^2$ of buprenorphin hydrochloride as calculated on buprenorphin and 43 ppm of residual ethyl acetate in the pressure sensitive tackifier layer was obtained.

After the plaster agent raw fabric was cut to a circular shape with a size of 9 cm$^2$, the hairless rat plastering test was conducted in the same manner as in Example 5-1, to obtain the results show in Table 5-1.

The content and the content ratio of the present plaster agent were found to be 2.5 mg and 7.5% by weight, respectively.

Example 5-3

According to the same procedure as in Example 5-2, except for using 0.2 part of a polyvinyl pyrrolidone K- 90 in place of the mixture of 0.2 part of HCO- 60 and 0.2 part of dissopropanolamine, a plaster agent raw fabric containing 2.8 g/m$^2$ of buprenorphin hydrochloride as calculated on buprenorphin and 37 ppm of residual ethy acetate in the pressure sensitive tackifier layer was obtained.

After the plaster agent raw fabric was cut to a circular shape with a size of 9 cm$^2$ (buprenorphin content 2.5 mg, content ratio 7.5% by weight), the hairless rat plastering test was conducted in the same manner as in Example 5-2, to obtain the results shown in Table 5-1.

Example 5-4

According to the same procedure as in Example 5-1, except for using 1.6 parts of buprenorphin hydrochloride in place of 1.5 parts of buprenorphin and 0.2 parts of diisopropanolamine in place of 0.2 part of HCO- 60, a pressure sensitive tackifier layer containing buprenorphin hydrochloride with a thickness of 30 µm, containing 1.4 g/m$^2$ of buprenorphin hydrocloride as calculated on buprenorphin, and 45 ppm of residual ethyl acetate in the pressure sensitive tackifier layer was obtained, and then cut to a size of 3 ×3 cm$^2$ (buprenorphin content 1.3 mg, content ratio 7.5% by weight).

On one surface of said pressure sensitive tackifier layer with a size of 9 cm$^2$ was pressure adhered a film (C) of an ethylene-vinyl acetate copolymer (vinyl acetate ratio 10%) with a size of 4 ×4 cm$^2$ and a thickness of 50 µm, to cover the whole surface, and further, a mixture of ethanol and hydroxypropyl cellulose (90:10) was placed at a central portion with a size of 3 ×3 cm$^2$ on the free surface of said ethylene-vinyl acetate copolymer film, an ethylene-vinyl acetate copolymer film (D) with a size of 4 ×4 cm$^2$ and a thickness of 50 µm was laminated with a 3.5 µm polyethylene terephthalate film and covered on the whole surface thereof. The ethylene-vinyl acetate copolymer film (C) and the ethylene-vinyl acetate copolymer film (D) were shaped into a bag to enclose the ethanol and hydroxypropyl cellulose therein, and the edges of the four sides were heat sealed to a width of about 5 mm, so that the ethanol and hydroxypropyl cellulose could not escape.

The results obtained by plastering buprenorphin hydrochloride having an ethanol reservoir thus obtained, in the same manner as in Example 5-1 are shown in Table 5-1. It was confirmed by the GC method that ethanol was slowly released through the ethylene-vinyl acetate copolymer film, from the ethanol reservoir of this Example.

TABLE 5-1

BN level in rat blood (average value of n = 2)

(Unit: ng/ml)

| | Preparation (by use of hollow fiber sample) | | | | Level in blood | | |
|---|---|---|---|---|---|---|---|
| | Kind of BN | Content[1] | Content ratio[2] | Absorption promoter[3] | before plastering | 2 hours after plastering | 8 hours after plastering | 24 hours after plastering |
| Example 5-1 | Free HCL | 2.6 | 7.5 | HCO-60 (1) | 0 | 6.8 | 11.2 | 8.0 |
| Example 5-2 | salt | 2.5 | 7.5 | HCO-60 (1) DIPA[4] | 0 | 8.3 | 11.9 | 4.5 |

TABLE 5-1-continued

BN level in rat blood (average value of n = 2)

(Unit: ng/ml)

| | | | | | Level in blood | | |
|---|---|---|---|---|---|---|---|
| | | | | | 2 hours | 8 hours | 24 hours |
| | Kind of BN | Content[*1] | Content ratio[*2] | Absorption promoter[*3] | before plastering | after plastering | after plastering | after plastering |
| Example 5-3 | " | 2.5 | 7.5 | PVP K-90 | 0 | 3.0 | 6.8 | 2.2 |
| Example 5-4 | " | 1.3 | 7.5 | DIPA (1) Ethanol reservoir | 0 | 1.7 | 10.4 | — |

[*1]mg
[*2]% by weight
[*3]% by weight of numeral in bracket
[*4]DIPA: diisopropanolamine

Example 5-5

In the same manner as in Example 5-1, except for not using HCO-60, a plaster agent with a size of 4.5 cm$^2$, a buprenorphin content of 1.3 mg, and a content ratio of 7.5% by weight was obtained.

The preparation obtained was plastered onto the back of a depilated hairless rat with a body weight of about 180 g, and 8 hours after plastering, the plaster agent was removed. The buprenorphin amount in the preparation after plastering was extracted with methanol and the quantitated by the HPLC method, and the buprenorphin amount absorbed during 8 hours plastering was estimated. The results are shown in Table 5-2.

Examples 5-6 –5-15

In the same manner as in Example 5-1, except for using buprenorphin hydrochloride in place of buprenorphin and the promoter shown in Table 5-2 in place of HCO-60, a plaster agent with a size of 4.5 cm$^2$, a buprenorphin content of about 1.3 mg, and a content ratio of 7.5% by weight was obtained.

For the plaster agents thus obtained, the plastering tests were practiced in the same manner as in Example 5-5, and from the buprenorphin concentration difference in the preparation before and after plastering, the amount of buprenorphin absorbed was estimated to obtain the results shown in Table 5-2.

It can be seen that buprenorphin is better absorbed than buprenorphin hydrochloride. Also, the hydrochloride had a very low subcutaneous absorption amount in the absence of absorption promoter. Nevertheless, when the preparations were plastered, the hairless rat exhibited symptoms which may be considered to be due to the pharmacological effect of buprenorphin, such as an extremely worsened response to external heat stimulation.

TABLE 5-2

Rat percutaneous absorption amount of BN (Unit: μg/8 hours)

Absorption promoter

| Preparation | Compound | Amount added (%) | Percutaneous Absorption amount |
|---|---|---|---|
| Example 5-5 (BN free) | None | — | 40 |
| Example 5-6 (BN HCl salt) | Propylene glycol | 1 | 132 |
| Example 5-7 (BN HCl salt) | Tween[R] 80 | 1 | 250 |
| Example 5-8 (BN HCl salt) | Isopropyl myristate | 1 | 195 |
| Example 5-9 (BN HCl salt) | Benzyl alcohol | 1 | 201 |
| Example 5-10 (BN HCl salt) | Diisopropanol amine | 1 | 44 |
| Example 5-11 (BN HCl salt) | Menthol | 5 | 55 |
| Example 5-12 (BN HCl salt) | Isosorbide nitrate | 5 | 149 |
| Example 5-13 (BN HCl salt) | HCO-60 | 0.5 | 159 |
| Example 5-14 (BN HCl salt) | HCO-60 | 1.0 | 139 |
| Example 5-15 (BN HCl salt) | None | — | 20 |

What is claimed is:

1. A method of preparing a plaster agent comprising:
   laminating one tackifier layer (layer b), a knitted fabric having a weight per unit area of 10 to 100 g/m$^2$ and a texture wherein the sum of a number of loops in the longitudinal and lateral directions thereof is 15 to 37 loops/cm (layer c) comprising hollow fibers having pores extending therethrough in the outer peripheral direction and substantially free from medicine and another tackifier layer (layer d) on one surface of a water impermeable or water semipermeable film (layer a) in an order of layers a, b, c, d, and
   using a tackifier layer containing at least one medicine selected from nitric acid esters, guayazulene, camphor, menthol, salicylic acid esters, hormones, analgesics and cardiac agents as at least one of said layer b and said layer d.

2. A method of preparing a plaster agent as claimed in claim 1, wherein a laminate comprising layer b laminated on one surface of layer a is prepared, a layer c is laminated on said layer b, and a layer d is laminated on said layer c.

3. A method of preparing a plaster agent as claimed in claim 1 or 2, wherein the medicine is at least one non-vaporizable medicine selected from hormones, analgesics, and cardiac agents.

4. A method of preparing a plaster agent comprising:

(1) impregnating a laminate having a water impermeable or water semipermeable film (layer a), one tackifier layer (layer b) containing substantially no vaporizable medicine or containing a small amount of a vaporizable medicine and laminated on the surface of said layer a, and a knitted fabric having a weight per unit area of 10 to 100 g/m² and a texture wherein the sum of a number of loops in the longitudinal and lateral directions thereof is 15 to 37 loops/cm (layer c) comprising pores extending therethrough in the outer peripheral direction and substantially free from medicine internally thereof and laminated on said layer b with a drug solution obtained by dissolving the vaporizable medicine in a volatile solvent on the surface of said layer c, (2) subsequently heating said laminate while the surface of said layer c is not in contact with the air, to thereby cause a migration of said vaporizable medicine in said knitted fabric portion to said layer b, and (3) laminating a second tackifier layer (layer d), which may also contain said vaporizable medicine, on said layer c.

5. A method of preparing a plaster agent as claimed in claim 4, wherein the medicine is at least one vaporizable medicine selected from nitric acid esters, guayazulene, camphor, menthol and salicylic acid esters.

6. A method of preparing a plaster agent comprising:

(1) impregnating a laminate having a water impermeable or water semipermeable film (layer a), one tackifier layer (layer b) containing substantially no vaporizable medicine or containing a small amount of a vaporizable medicine and laminated on the surface of said layer a, and a knitted fabric having a weight per unit area of 10 to 100 g/m² and a texture wherein the sum of a number of loops in the longitudinal and lateral directions thereof is 15 to 37 loops/cm (layer c) comprising pores extending therethrough in the outer peripheral direction and substantially free from medicine internally thereof and laminated on said layer b with a drug solution obtained by dissolving the vaporizable medicine in a volatile solvent on the surface of said layer c, (2) laminating a second tackifier layer (layer d), which may also contain said vaporizable medicine, on said layer c to obtain a laminate, and (3) heating said laminate to thereby cause a migration of said vaporizable medicine in said knitted fabric portion to said layer b and/or said layer d.

7. A method of preparing a plaster agent as claimed in claim 6, wherein the medicine is at least one vaporizable medicine selected from nitric acid esters, guayazulene, camphor, menthol, and salicylic acid esters.

8. A method of preparing a plaster agent as claimed in claim 1, wherein said nitric acid ester is isosorbide dinitrate, said hormone is at least one compound selected from the group consisting of estradiol, estradiol benzoate, estradiol dipropionate, estradiol valerate, and ethynyl estradiol, and said analgesic is buprenorphin.

* * * * *

UNITED STATES PATENT AND TRADEMARK OFFICE
CERTIFICATE OF CORRECTION

PATENT NO. : 6,294,045 B1
DATED : September 25, 2001
INVENTOR(S) : Hidaka, Osafumi et al.

It is certified that error appears in the above-identified patent and that said Letters Patent is hereby corrected as shown below:

<u>Title page,</u>
Item [30], please correct to read:

-- [30]  Foreign Application Priority Data
Feb. 28, 1989 (JP) ................................. 1-45178
June 28, 1989 (JP) ................................. 1-166040
June 28, 1989 (JP).. ................................. 1-166041
June 28, 1989 (JP)................................. 1-166042
Aug. 22, 1989 (JP) ................................. 1-214162
Feb. 28, 1990 (WO) ........................ PCT/JP90/00263 --

Signed and Sealed this

Nineteenth Day of November, 2002

*Attest:*

*Attesting Officer*

JAMES E. ROGAN
*Director of the United States Patent and Trademark Office*